US011633380B2

(12) United States Patent
Bakewell et al.

(10) Patent No.: US 11,633,380 B2
(45) Date of Patent: *Apr. 25, 2023

(54) USE OF TRANS-[TETRACHLOROBIS(1H-INDAZOLE) RUTHENATE(III)] FOR THE TREATMENT OF CANCER

(71) Applicant: Bold Therapeutics, Inc., Vancouver (CA)

(72) Inventors: Suzanne Bakewell, Tampa, FL (US); Jyothi Sethuraman, Riverview, FL (US)

(73) Assignee: BOLD THERAPEUTICS, INC., Vancouver (CA)

( * ) Notice: Subject to any disclaimer, the term of this patent is extended or adjusted under 35 U.S.C. 154(b) by 263 days.

This patent is subject to a terminal disclaimer.

(21) Appl. No.: 17/036,628

(22) Filed: Sep. 29, 2020

(65) Prior Publication Data
US 2021/0085647 A1 Mar. 25, 2021

Related U.S. Application Data

(62) Division of application No. 16/081,554, filed as application No. PCT/US2017/020209 on Mar. 1, 2017, now Pat. No. 10,821,095.

(60) Provisional application No. 62/301,786, filed on Mar. 1, 2016.

(51) Int. Cl.
*A61K 31/416* (2006.01)
*A61K 45/06* (2006.01)
*A61K 39/395* (2006.01)
*C07K 16/28* (2006.01)
*A61K 31/555* (2006.01)
*A61P 35/00* (2006.01)
*A61K 31/7068* (2006.01)
*A61K 39/00* (2006.01)

(52) U.S. Cl.
CPC .......... *A61K 31/416* (2013.01); *A61K 31/555* (2013.01); *A61K 31/7068* (2013.01); *A61K 39/3955* (2013.01); *A61K 39/39541* (2013.01); *A61K 45/06* (2013.01); *A61P 35/00* (2018.01); *C07K 16/2818* (2013.01); *A61K 2039/505* (2013.01); *C07K 2317/73* (2013.01)

(58) Field of Classification Search
CPC .................................................. A61K 31/416
USPC ........................................................ 514/403
See application file for complete search history.

(56) References Cited

U.S. PATENT DOCUMENTS 9,089,578 B2 7/2015 Sheshbaradaran et al.
10,821,095 B2 * 11/2020 Bakewell ........... A61K 39/3955
2013/0129840 A1 5/2013 Sheshbaradaran et al.

FOREIGN PATENT DOCUMENTS

WO WO-2008/154553 A1 12/2008
WO WO-2012/012305 1/2012
WO WO-2016/029073 A2 2/2016

OTHER PUBLICATIONS

Bond-Smith, BMJ 2012;344:e2476 doi: 10.1136/bmj.e2476 (Published May 16, 2012).*
Lee "Glucose-regulated proteins in cancer: molecular mechanisms and therapeutic potential," Nature Reviews Cancer, 14(4), pp. 263-276 (2014).
Trondl et al., "NKP-1339, a first-in-class anticancer drug showing mild side effects and activity in patients suffering from advanced refractory cancer," BMC Pharmacology & Toxicology, 13(Suppl. 1), Article No. A82 (2012).
Chiou et al., "Glucose-Regulated Protein 78 is a Novel Contributor to Acquisition of Resistance to Sorafenib in Hepatocellular Carcinoma," Ann. Surg. Oncol., 17(2), pp. 603-612 (2010).
Fernandez et al., "Overexpression of the glucose-regulated stress gene GRP78 in malignant but not benign human breast lesions," Breast Cancer Res. Treat., 59(1), pp. 15-26 (2000).
Gifford et al., "Expression of GRP78, Master Regulator of the Unfolded Protein Response, Increas-es Chemoresistance in Pancreatic Ductal Adenocarcinoma," Molecular Cancer Therapeutics, 15, pp. 1043-1052 (2016).
Heffeter et al., "The ruthenium compound KP1339 potentiates the anticancer activity of sorafenib in vitro and in vivo," European Journal of Cancer, 49(15), pp. 3366-3375 (Oct. 1, 2013).
Huergo-Zapico et al., "Expression of ERp5 and GRP78 on the membrane of chronic lymphocytic leukemia cells: association with soluble MICA shedding," Cancer Immunol. Immunother., 61, pp. 1201-1210 (2012).
International Search Report and Written Opinion for International Application No. PCT/US17/20209, dated Jun. 16, 2017 (9 pages).
Jiang et al., "Glucose-regulated protein 78 antagonizes cisplatin and adriamycin in human melanoma cells," Carcinogenesis, 30(2), pp. 197-204 (2009).
Kern et al., "GRP-78 secreted by tumor cells blocks the antiangiogenic activity of bortezomib," Blood, 114(18), pp. 3960-3967 (2009).

(Continued)

*Primary Examiner* — Nizal S Chandrakumar
(74) *Attorney, Agent, or Firm* — Mintz, Levin, Cohn, Ferris, Glovsky and Popeo, P.C.

(57) ABSTRACT

IT-139, sodium trans-[tetrachlorobis(1H-indazole)ruthenate (III)], is an intravenously administered small molecule compound. In preclinical anti-tumor and mechanism of action studies, IT-139 showed activity against a broad range of tumor types, including those which are resistant to standard anti-cancer agents (e.g., platinums, vinca alkaloids, taxanes, anthracyclines). This activity is believed to arise from IT-139's novel mechanism of action that targets the GRP78 pathway. It was found that up-regulation of GRP78 is a key cancer cell survival pathway. Downregulation of GRP78 using IT-139 removes this resistance pathway allowing for chemotherapy and immuno-oncology agents to be more effective in treating cancer.

10 Claims, 17 Drawing Sheets

(56) References Cited

OTHER PUBLICATIONS

Lai et al., "Endoplasmic Reticulum Stress: Signaling the Unfolded Protein Response," Physiology (Bethesda), 22, pp. 193-201 (2007).
Lee et al., "GRP78 as a Novel Predictor of Responsiveness to Chemotherapy in Breast Cancer," Cancer Res., 66(16), pp. 7849-7853 (2006).
Luo et al., "GRP78/BIP Is Required for Cell Proliferation and Protecting the Inner Cell Mass from Apoptosis During Early mouse Embryonic Development," Mol. Cell Biol., 26(15), pp. 5688-5697 (2006).
Ma and Hendershot, "The role of the unfolded protein response in tumour development: friend or foe?" Nat. Rev. Cancer, 4(12) pp. 966-977 (2004).
Mahadevan et al., "Cell-Extrinsic Effects of Tumor ER Stress Imprint Myeloid Dendritic Cells and Impair CD8+ T Cell Priming," PLoS One, 7(12), e51845, 13 pages (2012).
Mhaidat et al., "Inhibition of MEK sensitizes paclitaxel-induced apoptosis of human colorectal cancer cells by downregulation of GRP78," Anti-Cancer Drugs, 20(7) pp. 601-606 (2009).
Pyrko et al., "The Unfolded Protein Response Regulator GRP78/BIP as a Novel Target for Increasing Chemosensitivity in Malignant Gliomas," Cancer Res., 67(20), pp. 9809-9816 (2007).
Reddy et al., "Endoplasmic Reticulum Chaperone Protein GRP78 Protects Cells from Apoptosis Induced by Topoisomerase Inhibitors: Role of ATP Binding Site in Suppression of CASPASE-7 Activation," J. Biol. Chem., 278(23), pp. 20915-20924 (2003).
Sitia and Braakman, "Quality control in the endoplasmic reticulum protein factory," Nature, 426(6968) pp. 891-894 (2003).
Triantafilou et al., "Major Histocompatibility Class One Molecule Associates With Glucose Regulat-ed Protein (GRP) 78 on the Cell Surface," Hum. Immunol., 62, pp. 764-770 (2001).
Tsunemi et al., "Proteomics-based identification of a tumor-associated antigen and its correspond-ing autoantibody in gastric cancer," Oncol. Rep., 23(4), pp. 949-956 (2010).
Virrey et al., "Stress Chaperone GRP78/BIP Confers Chemoresistance to Tumor-Associated Endo-thelial Cells," Mol. Cancer Res., 6(8), pp. 1268-1275 (2008).
Wang et al., "Blockade of GRP78 sensitizes breast cancer cells to microtubules-interfering agents that induce the unfolded protein response," J. Cell Mol. Med., 13(9B), pp. 3888-3897 (2009).
Wang et al., "Different Induction of GRP78 and CHOP as a Predictor of Sensitivity to Proteasome Inhibitors in Thyroid Cancer Cells," Endocrinology, 148(7), pp. 3258-3270 (2007).
Wang et al., "Down-regulation of GRP78 is associated with the sensitivity of chemotherapy to VP-16 in small cell lung cancer NCI-H446 cells," BMC Cancer, 8, pp. 372 (2008).
Xing et al., "Overexpression of glucose-regulated protein 78 in colon cancer," Clin. Chim. Acta, 364(1-2) pp. 308-315 (2006).
Xu et al., "Endoplasmic reticulum stress: cell life and death decisions," J. Clin. Invest., 115(10), pp. 2656-2664 (2005).
Zhang et al., "Association of elevated GRP78 expression with increased lymph node metastasis and poor prognosis in patients with gastric cancer," Clin. Exp. Metastasis, 23(7-8), pp. 401-410 (2006).
Burris et al., "Safety and activity of IT-139, a ruthenium-based compound, in patients with advanced solid tumours: a first-in-human, open-label, dose-escalation phase I study with expansion cohort," ESMO Open, 1:e000154, 8 pages (2016).
Trondl et al., "NKP-1339, the first ruthenium-based anticancer drug on the edge to clinical application," Chem. Sci., 5, pp. 2925-2932 (2014).
Mahalingam et al., "The combination of intravenous Reolysin and gemcitabine induces reovirus replication and endoplasmic reticular stress in a patient with KRAS-activated pancreatic cancer," BMC Cancer, 15(513) 5 pages (2015).
Gong and Mita "Activated Ras signaling pathways and reovirus oncolysis: an update on the mechanism of preferential reovirus replication in cancer cells," Frontiers in Oncology | Molecular and Cellular Oncology, vol. 4 (article 167), pp. 1-7 (2014).

\* cited by examiner

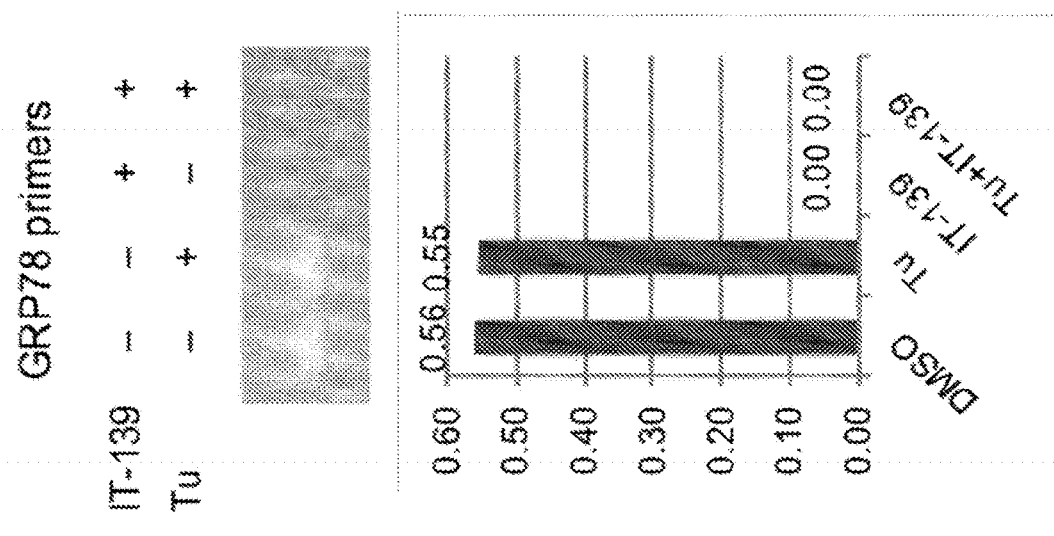
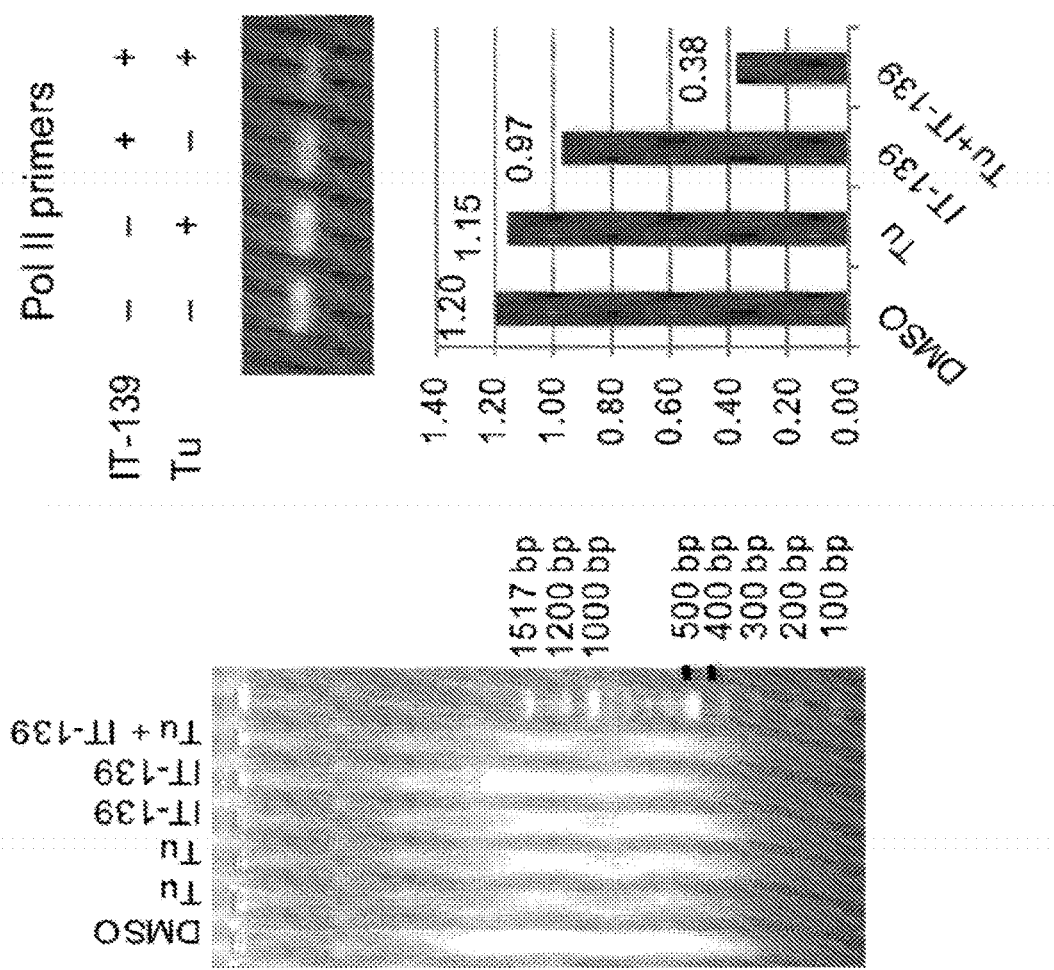

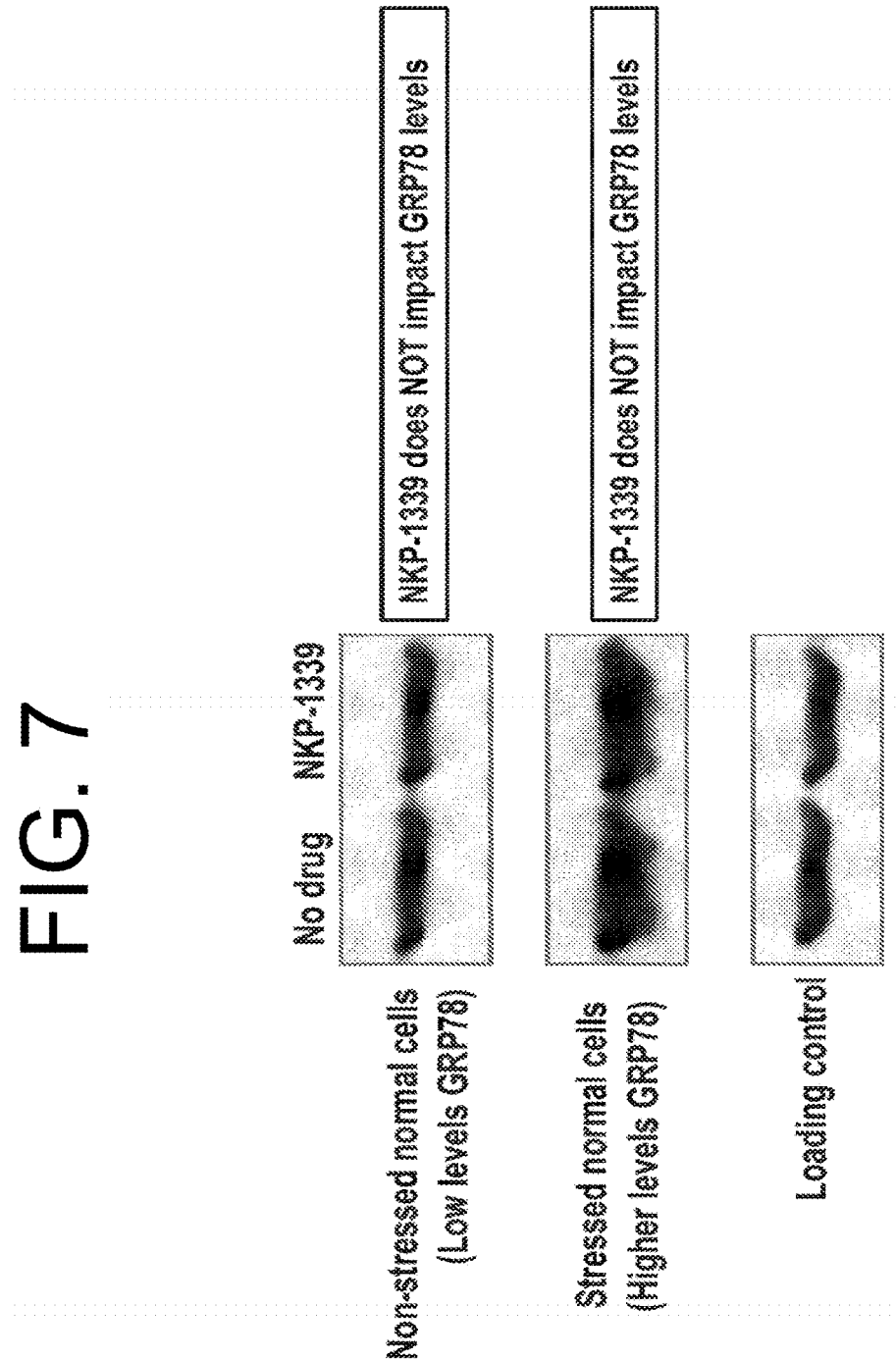

USE OF TRANS-[TETRACHLOROBIS(1H-INDAZOLE) RUTHENATE(III)] FOR THE TREATMENT OF CANCER

This application is a Divisional of U.S. patent application Ser. No. 16/081,554, filed Aug. 31, 2018, which is a U.S. National Phase Application of PCT International Application No. PCT/US2017/020209, filed Mar. 1, 2017, which is an International Application of and claims the benefit of priority to U.S. patent application Ser. No. 62/301,786, filed Mar. 1, 2016, each of which is incorporated herein in their entirety for all purposes.

FIELD OF THE INVENTION

BACKGROUND OF THE INVENTION

Many advances have been made in the treatment of cancers in recent years. However, in most instances of metastatic disease, treatment is not curative because tumor cells develop mechanisms to overcome and survive the damage caused by the anti-cancer agent. Targeting and overcoming these survival/resistance mechanisms of the tumor cell is an area of anti-cancer targeting that is the subject of active research. Accordingly, there remains an unmet need to develop therapeutics to treat cancer, and, in particular, resistance.

SUMMARY OF THE INVENTION

It has now been found that compounds of the present invention, and compositions thereof, are useful for treating cancer, and particularly, are useful for targeting survival and resistance mechanisms of tumor cells.

More specifically, it has now been found that IT-139 suppresses the stress up-regulation of GRP78 in tumor cells. This effect is specific to tumor cells, as IT-139 does not affect GRP78 expression in normal cells. Treatment of normal cells under non-stressed and stressed conditions with IT-139, showed that: 1) IT-139 does not effect the basal GRP78 levels in non-stressed normal cells; and 2) IT-139 does not effect GRP78 up-regulation due to stress in these same normal cells. Therefore it is believed that IT-139 does not impact GRP78 levels in normal cells regardless of stress conditions.

BRIEF DESCRIPTION OF THE DRAWINGS

FIGS. 1A-B depict GRP78 protein levels before and after treatment with IT-139 in: FIG. 1A unstressed cells; and FIG. 1B cells stressed with thapsigargin.

FIGS. 2A-B depict GRP78 mRNA levels before and after treatment with IT-139 in: FIG. 2A unstressed cells; and FIG. 2B cells stressed with thapsigargin.

FIG. 4A-B depict transmission electron microscopy images of HCT116 cells in: FIG. 4A controlled, untreated cells; and FIG. 4B HCT116 cells treated with IT-139.

FIG. 5A-C depicts effects of IT-139 on RNA Polymerase II Binding to GRP78 promoter in: 5A chip seq results; 5B quantification of Pol II primers by gel electrophoresis; and 5C quantification of GRP78 primers.

FIG. 6A-B depict immunohistochemistry staining of HT-29 tumors (ex vivo) treated with: FIG. 6A saline; and FIG. 6B IT-139.

FIG. 7 depicts treatment of kidney 293T cells in stressed and non-stressed conditions, with and without IT-139 treatment.

FIG. 8A-B depict treatment of kidney 293T cells in stressed and non-stressed conditions, with and without IT-139 treatment with respect to: FIG. 8A GRP78 mRNA levels; and FIG. 8B relative GRP78 mRNA expression.

DETAILED DESCRIPTION OF CERTAIN EMBODIMENTS OF THE INVENTION

1. General Description

Figure 1A:
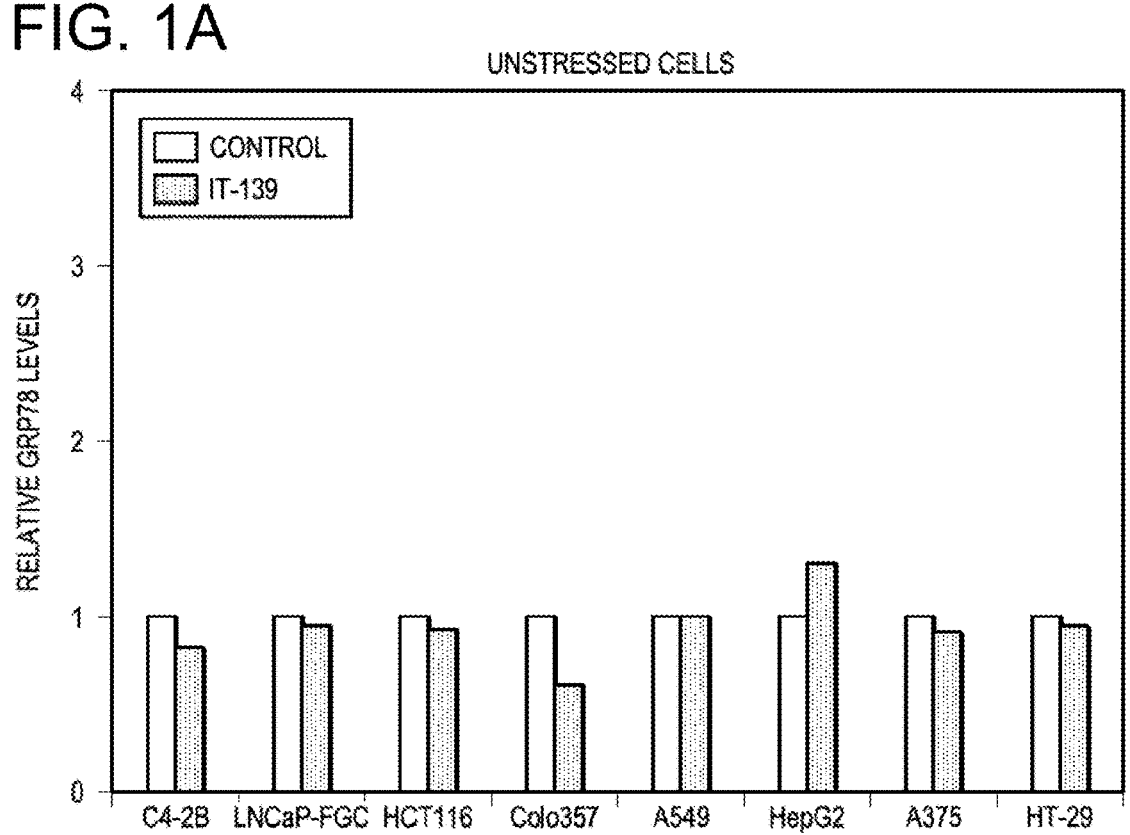

IT-139, sodium trans-[tetrachlorobis(1H-indazole)ruthenate(III)], is an intravenously administered small molecule compound. IT-139 is also known as KP1339 or NKP1339. In preclinical anti-tumor and mechanism of action studies, IT-139 showed activity against a broad range of tumor types, including those which are resistant to standard anti-cancer agents (e.g., platinums, vinca alkaloids, taxanes, anthracyclines). This activity is believed to arise from IT-139's novel mechanism of action, targeting the GRP78 pathway.

GRP78 (glucose regulated protein 78), also referred to as BiP or HSPA5 is a master-regulator of the endoplasmic reticulum (ER) stress response. It is also plays a critical role in tumor cell survival, anti-apoptosis and therapeutic resistance. In normal cells, GRP78 is found at low levels and located in the lumen of the endoplasmic reticulum. In stressed cells, GRP78 is significantly up-regulated and also found outside the ER in the cell cytoplasm, the nucleus, in the mitochondria, on the cell surface and secreted. The elevation of GRP78 expression in a wide variety of cancer types has been correlated with increased tumor cell proliferation, metastasis, angiogenesis, and tumor cell survival and resistance. High levels of GRP78 protein have been correlated with resistance to agents such as cisplatin, 5-FU, temozolomide, vinblastine, paclitaxel, bortezomib, sorafenib, camptothecin, etoposide, and doxorubicin. Furthermore, treatment of tumor cell lines with several of these agents results in additional up-regulation of GRP78 protein. In contrast to these anti-cancer drugs, IT-139 suppresses GRP78 up-regulation in tumor cells. IT-139 suppresses GRP78 transcription. This suppression is selective to tumor cells and is most pronounced in tumor cells under stress. IT-139 has no effect on GRP78 levels in normal cells whether under non-stressed or stressed conditions. As GRP78 up-regulation is one of the key causes of resistance, IT-139 was expected to show synergy when combined with other anti-cancer agents. Preclinical studies show that IT-139 has marked synergy when used in combination with all different classes of anti-cancer drugs tested to date.

GRP78 is a member of the Hsp70 family of heat shock proteins. In normal cells, GRP78 is localized predominantly in the endoplasmic reticulum (EndRet), where it facilitates the correct folding and assembly of proteins, including the translocation across the ER membrane and the targeting of misfolded proteins for degradation. See Sitia, R. and I. Braakman, *Quality control in the endoplasmic reticulum protein factory*. Nature, 2003. 426(6968): p. 891-4 and Xu, C., B. Bailly-Maitre, and J. C. Reed, *Endoplasmic reticulum stress: cell life and death decisions*. J Clin Invest, 2005. 115(10): p. 2656-64. Normal unstressed cells have low levels of mis-folded proteins and express low basal levels of GRP78. Under conditions of stress, higher levels of misfolded proteins are generated and the unfolded protein response (UPR) is activated. The UPR is mediated through three EndRet transmembrane receptors: protein kinase RNA-like endoplasmic reticulum kinase (PERK), activating transcription factor 6 (ATF6) and inositol-requiring enzyme 1 (IRE1). In unstressed cells, all three ER stress chaperones are maintained in an inactive form by the binding of GRP78. See Ma, Y. and L. M. Hendershot, *The role of the unfolded protein response in tumour development: friend or foe?* Nat Rev Cancer, 2004. 4(12): p. 966-77.

During stress, the number of misfolded proteins increases and GRP78 binds to them, releasing these transmembrane proteins, resulting in the initiation of a cascade of downstream activities including translation attenuation and up-regulation of ER stress target genes. See Lai, E., T. Teodoro, and A. Volchuk, *Endoplasmic reticulum stress: signaling the unfolded protein response*. Physiology (Bethesda), 2007. 22: p. 193-201. Through these functions, GRP78 is a master regulator of cell survival under conditions of stress.

In vivo models show that homozygous GRP78 (−/−) knock-outs are embryonically lethal, while heterozygous GRP78 (+/−) knock-out mice develop and function normally. These data suggest that some GRP78 is required for embryogenesis but normal cells can tolerate a high degree of GRP78 down-regulation without adverse effects. See Luo, S., et al., *GRP78/BiP is required for cell proliferation and protecting the inner cell mass from apoptosis during early mouse embryonic development*. Mol Cell Biol, 2006. 26(15): p. 5688-97.

In tumor cells, GRP78 assumes the role of a key tumor cell survival and resistance factor. GRP78 in cancer cells differs from normal cells in that GRP78 levels are significantly higher in tumor cells than in normal stressed cells, and the pattern of GRP78 localization differs from that of normal stressed cells. Unlike normal cells where GRP78 remains mainly confined to the EndRet, tumor cells have significant levels of GRP78 in the cytoplasm, nucleus, mitochondria, and cell surface. In addition, tumor cells secrete GRP78 into the peritumoral milieu. The combination of the increased levels and aberrant localization of GRP78 in cancer cells gives rise to increased tumor cell proliferation, Elevated GRP78 expression levels in tumors has been shown in a wide variety of cancer types including lung, gastric, breast, hepatocellular, thyroid, melanoma, glioma, colorectal, pancreatic, bladder and various leukemias (Table 1). In these tumor types, the method for detection of GRP78 were variable, utilizing immunohistochemistry (IHC) analysis, western blot analysis for GRP78 protein levels, northern blot analysis, or RT-PCR for GRP78 mRNA levels in either tumor derived cell lines or in patient tumor specimens.

In the tumor biopsy studies, GRP78 expression level in tumor cells was elevated compared to adjacent non-cancerous tissue.

In a hepatocellular carcinoma (HCC) study, GRP78 mRNA was significantly higher in 11 of 13 HCC tissues compared to the adjacent non-cancerous tissues ($p<0.05$) [14]. In addition, the sensitivity of HCC cells to sorafenib is correlated to level of GRP78 as determined by GRP78 siRNA experiments. See Chiou, J. F., et al., *Glucose-regulated protein 78 is a novel contributor to acquisition of resistance to sorafenib in hepatocellular carcinoma*. Ann Surg Oncol, 2010. 17(2): p. 603-12.

In brain tumors, IHC and Western blot studies reveal that GRP78 is significantly elevated in malignant glioma specimens and human malignant glioma cell lines, compared to normal adult brain. The studies also showed high GRP78 levels correlated with increased rate of tumor cell proliferation. See Pyrko, P., et al., *The unfolded protein response regulator GRP78/BiP as a novel target for increasing chemosensitivity in malignant gliomas*. Cancer Res, 2007. 67(20): p. 9809-16 and Virrey, J. J., et al., *Stress chaperone GRP78/BiP confers chemoresistance to tumor-associated endothelial cells*. Mol Cancer Res, 2008. 6(8): p. 1268-75.

In a melanoma study using fresh biopsy isolates, melanoma tumor cells were shown to express elevated GRP78 compared with normal melanocytes. Furthermore, the fresh melanoma tumor isolates had up to 4 times greater levels of GRP78 by Western blot compared to cultured melanoma cell lines. See Jiang, C. C., et al., *Glucose-regulated protein 78 antagonizes cisplatin and adriamycin in human melanoma cells*. Carcinogenesis, 2009. 30(2): p. 197-204.

In a breast cancer study, approximately 65% of pretreatment tumor specimens expressed high levels of GRP78 by IHC. See Lee, E., et al., *GRP78 as a novel predictor of responsiveness to chemotherapy in breast cancer*. Cancer Res, 2006. 66(16): p. 7849-53. This agrees with a previous published report by Fernandez, et al, which demonstrated a 1.8 to 20 fold overexpression of GRP78 mRNA in 3/5 estrogen receptor positive breast tumors and 6/9 estrogen receptor negative breast tumors compared to 0/5 benign breast lesions. See Fernandez, P. M., et al., *Overexpression of the glucose-regulated stress gene GRP78 in malignant but not benign human breast lesions*. Breast Cancer Res Treat, 2000. 59(1): p. 15-26.

In a study of thyroid cancer, Wang et al showed thyroid cancer cells express high basal levels of GRP78 as assessed by real-time RT-PCR and Western blot. In addition, the sensitivity of thyroid cancer cells to proteosome inhibition is correlated to the level of GRP78 as determined by GRP78 siRNA experiments. Wang, H. Q., et al., *Different induction of GRP78 and CHOP as a predictor of sensitivity to proteasome inhibitors in thyroid cancer cells*. Endocrinology, 2007. 148(7): p. 3258-70.

Correlation of high GRP78 expression level in tumor biopsy with poor survival has been shown in gastric and colorectal cancers. See Xing, X., et al., *Overexpression of* glucose-regulated protein 78 in colon cancer. Clin Chim Acta, 2006. 364(1-2): p. 308-15. Zhang, et al., report IHC analysis of biopsies from 86 patients with primary gastric cancer demonstrating that GRP78 was overexpressed in the tumor cells when compared with the adjacent tumor-free gastric mucosa. See Zhang, J., et al., *Association of elevated GRP78 expression with increased lymph node metastasis and poor prognosis in patients with gastric cancer. Clin Exp Metastasis,* 2006. 23(7-8): p. 401-10. The intensity of tumor GRP78 staining was graded as negative, weak or strong. The level of GRP78 expression levels showed a significant correlation with median overall survival with median survival for patients whose tumors stained as negative, weak or strong of 2489, 1242, and 432 days, respectively (p<0.001 for overall survival of negative versus strong GRP78 tumor expression). Similarly, GRP78 expression in lymph nodes correlated with poor overall survival (p=0.037 for overall survival of negative versus any GRP78 expression in lymph nodes).

In a more recent study, Tsunemi, et al, assessed the localization of GRP78 expression in gastric cancer tissue and normal gastric mucosa by IHC. In normal gastric mucosa, GRP78 staining was occasionally observed in the deep propria glands, but not in the superficial epithelium. In gastric cancer tissue, GRP78 was expressed at high levels in the cytoplasm of cancer cells regardless of the depth from the surface. In the same study, circulating GRP78 protein was assessed in the serum of both patients with gastric cancer and normal individuals. Western blots against recombinant GRP78 showed reactivity in sera from 17/60 (28.3%) patients with gastric cancer and 0/20 (0.0%) of healthy individuals. See Tsunemi, S., et al., *Proteomics-based identification of a tumor-associated antigen and its corresponding autoantibody in gastric cancer. Oncol Rep,* 2010. 23(4): p. 949-56.

IT-139 was selected for its activity in various resistant tumor cell lines, and therefore its target(s) were expected to be those that affect resistance. The primary target of IT-139 has now been identified to be GRP78. It has now been found that, surprisingly, IT-139 suppresses the stress up-regulation of GRP78 in tumor cells. This effect is specific to tumor cells, as IT-139 does not affect GRP78 expression in normal cells. Treatment of normal cells under non-stressed and stressed conditions with IT-139, showed that: 1) IT-139 does not effect the basal GRP78 levels in non-stressed normal cells; and 2) IT-139 does not effect GRP78 up-regulation due to stress in these same normal cells. Therefore it is believed that IT-139 does not impact GRP78 levels in normal cells regardless of stress conditions.

Without wishing to be bound by any particular theory, it is believed that IT-139 is not a general inhibitor of the UPR but rather a specific suppressor of GRP78 induction. The main pathway of GRP78 induction is via transcription. IT-139 suppression of GRP78 is at the transcriptional level in a dose dependent manner, as seen by Northern blot analysis of tumor cells treated with IT-139. In some embodiments, the present invention encompasses the finding that IT-139 suppresses the induction of GRP78 by stress inducing agents.

It was surprisingly found that IT-139 does not block other arms of the UPR such as induction XBP-1 spliced form, induction, processing and nuclear import of ATF6, and phosphorylation of eIF2a. IT-139 therefore causes ER stress and part of the UPR, but suppresses induction of GRP78 (the survival arm of UPR).

The IT-139 suppression of GRP78 induction at the transcriptional level is confirmed by GRP78 promoter studies. Regulation of GRP78 protein levels in the cell is primarily via transcriptional control due to the fact that the GRP78 promoter contains multiple copies of endoplasmic reticulum stress elements (ERSE). ERSEs are binding sites of the stress induced transcription factors. IT-139 has been to shown to suppress stress-induction of the GRP78 promoter fragment (−169 to −29; contains 3 ERSEs) linked to a luciferase reporter gene.

Induction of GRP78 is the cell's survival response under conditions of stress. It is the attempt of the cell to repair itself and prevent apoptosis. GRP78 induction is therefore seen when cells are stressed/dying. IT-139 suppression of GRP78 in tumor cells is most prominent in stressed tumor cells. Tumor cells in vivo are always undergoing various kinds of stress. In non-stressed tumor cells in vitro, IT-139 suppresses GRP78 levels to varying levels in different tumor lines.

High levels of GRP78 protein have been correlated with resistance to agents such as cisplatin (Jiang, C. C., et al., *Glucose-regulated protein 78 antagonizes cisplatin and adriamycin in human melanoma cells.* Carcinogenesis, 2009. 30(2): p. 197-204), 5-FU (Pyrko, P., et al., *The unfolded protein response regulator GRP78/BiP as a novel target for increasing chemosensitivity in malignant gliomas.* Cancer Res, 2007. 67(20): p. 9809-16), temozolomide (Pyrko 2007), vinblastine (Wang, J., et al., *Blockade of GRP78 sensitizes breast cancer cells to microtubules-interfering agents that induce the unfolded protein response.* J Cell Mol Med, 2009. 13(9B): p. 3888-97), paclitaxel (Mhaidat, N. M., et al., *Inhibition of MEK sensitizes paclitaxel-induced apoptosis of human colorectal cancer cells by downregulation of GRP78.* Anticancer Drugs, 2009. 20(7): p. 601-6), bortezomib (Kern, J., et al., *GRP-78 secreted by tumor cells blocks the antiangiogenic activity of bortezomib.* Blood, 2009. 114(18): p. 3960-7), sorafenib (Chiou, J. F., et al., *Glucose-regulated protein 78 is a novel contributor to acquisition of resistance to sorafenib in hepatocellular carcinoma.* Ann Surg Oncol, 2010. 17(2): p. 603-12), camptothecin (Reddy, R. K., et al., *Endoplasmic reticulum chaperone protein GRP78 protects cells from apoptosis induced by topoisomerase inhibitors: role of ATP binding site in suppression of caspase-7 activation.* J Biol Chem, 2003. 278(23): p. 20915-24), etoposide (Wang, Y., et al., *Downregulation of GRP78 is associated with the sensitivity of chemotherapy to VP-16 in small cell lung cancer NCI-H446 cells.* BMC Cancer, 2008. 8: p. 372) and doxorubicin (Jiang, C. C., et al., *Glucose-regulated protein 78 antagonizes cisplatin and adriamycin in human melanoma cells.* Carcinogenesis, 2009. 30(2): p. 197-204). Furthermore, treatment of tumor cell lines with several of these agents further up-regulates levels of GRP78 protein. See Jiang 2009 and Reddy 2003. This additional up-regulation of GRP78 induced by anticancer agents is thought to be a significant determinant of tumor cell survival and resistance. That IT-139 preferentially prevents GRP78 induction in "stressed" tumor cells, suggested that IT-139 would be synergistic when used in combination with anti-cancer agents of many different classes.

Multiple GRP78 transcription factors are effected following stress induction, including NF-Y, TFII-I, ATF6α, and YY-1. NF-Y binding is preserved in stressed and non-stressed GRP78 transcription. TFII-I binding is enhanced in stressed transcription. ATF6 is cleaved to ATF6α within 1 h of thapsigargin (Tg) stress treatment and results only after ER stress. This complex (ATF6α/YY1) recruits PRMT1 to the promoter along with methylated histone H4, p300, GCN5 and histone acetyltransferases. ATF6α functions (at least in part) by recruiting a collection of RNA polymerase II coregulatory complexes, including the Mediator and multiple histone acetyltransferase complexes (Spt-Ada-Gcn5 acetyltransferase (SAGA) and Ada-Two-A-containing (ATAC) complexes) to the ER stress response enhancer elements. Without wishing to be bound to any particular theory, we propose that IT-139 inhibits to loading of this POL II complex on the GRP78 promoter region.

One embodiment of the present invention is that IT-139's mechanism of action is an effect on the transcription of GRP78. Another embodiment of the present invention is that IT-139 inhibits the stress-induced transcription of GRP78. Transcriptional activation of GRP78 is an indicator of the unfolded protein response. UPR induces specific acetylation and methylation modification of nucleosomes. It is theorized that the ERSE is the most critical element mediating the stress induction of the GRP78 promoter.

Another aspect of the present invention is a method of treating a cancer in a subject in need thereof, comprising administering IT-139, or a pharmaceutically acceptable composition thereof, in combination with one or more immuno-oncology therapeutics. Tumor-borne ER stress imprints ab initio BMDC to a phenotype that recapitulates several of the inflammatory/suppressive characteristics ascribed to tumor-infiltrating myeloid cells, highlighting the tumor UPR as a critical controller of anti-tumor immunity and a new target for immune modulation in cancer. (See Mahadevan et al. PlosONe December 2012) Shedding of the NKG2D ligand, MICA, by chronic lymphocytic leukemia cells can be induced upon translocation of the endoplasmic reticulum-resident proteins ERp5 and GRP78 to the tumor cell surface. (See Cancer Immunol Immunother (2012) 61:1201) Surface LAP/TGF-β forms a complex with GRP78, and knockdown of GRP78 reduces the expression levels of surface LAP/TGF-β on Tregs. (See *Hum. Immunol.* 62, 764-770, 2001) Therefore, without wishing to be bound to any theory, we believe that combination therapy comprising IT-139 and an immuno-oncology agent will result in a more effective treatment than the immuno-oncology agent alone.

2. Definitions

As described herein, the phrase immuno-oncology agent refers to any cancer immunotherapy agent wherein the immune system is leveraged to treat cancer. Such agents include, but are not limited to, antibodies, PD-1 therapies, PD-L1 therapies, cytokine therapeutics, and checkpoint inhibitors. Specific examples include, but are not limited to, nivolumab, alemtuzumab, atezolizumab, ipilimumab, ofatumumab, pembrolizumab, rituximab, interferon, and interleukin. Targets of immune-oncology agents include, but are not limited to, CD52, PD-L1, CTLA4, CD20, or the PD-1 receptor.

As described herein, the phrase chemotherapy agent or chemotherapeutic agent describes a chemical substance used to treat cancer. Such agents include cytotoxic and cytostatic drugs. A chemotherapy agent or chemotherapeutic agent may also refer to an antibody or a monoclonal antibody (MAB). Classes of chemotherapeutic agents include, but are not limited to: taxanes, anthracyclines, platinum containing drugs, epothilones, anti-mitotic agents, camptothecins, folic acid derivatives, HDAC inhibitors, mitotic inhibitors, microtubule stabilizers, DNA intercalators, topoisomerase inhibitors, or molecularly targeted therapeutics. The phrase chemotherapy agent or chemotherapeutic agent may also refer to one or more chemical substances combined together to treat cancer. One non-limiting example of this may include gemcitabine and nanoparticle albumin paclitaxel.

As used herein, the term IT-139 refers to sodium trans-[tetrachlorobis(1H-indazole)ruthenate(III)]. IT-139 is also known as KP1339 or NKP1339.

Vinca alkaloids are well known in the literature and are a set of anti-mitotic agents. Vinca alkaloids include vinblastine, vincristine, vindesine, and vinorelbine, and act to prevent the formation of microtubules. Exemplary vinca alkaloids are shown below.

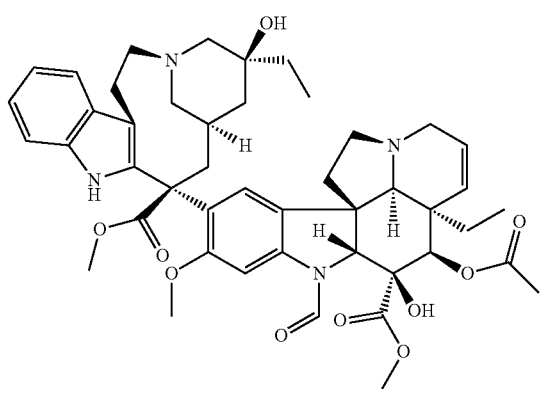

Vincristine

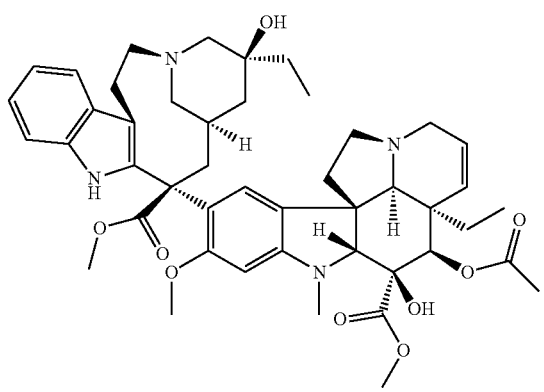

Vinblastine

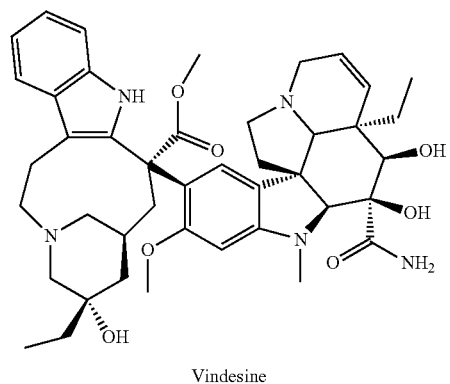

Vindesine

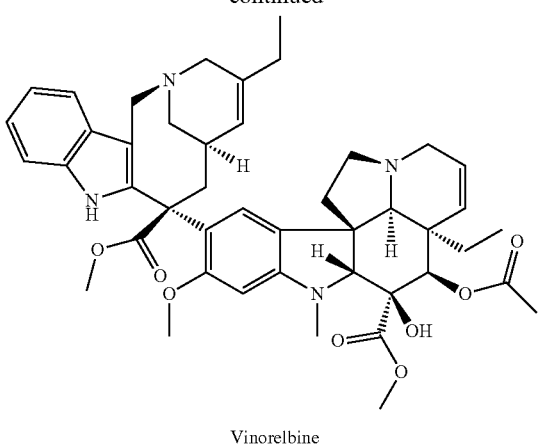

Vinorelbine

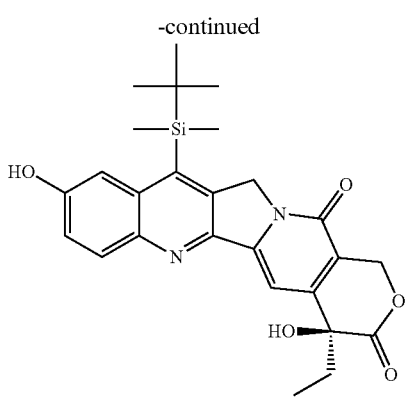

DB 67

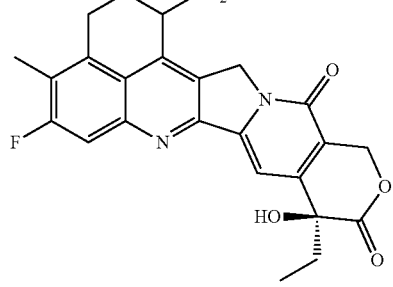

Exatecan

The antitumor plant alkaloid camptothecin (CPT) is a broad-spectrum anticancer agent that targets DNA topoisomerase I. Although CPT has shown promising antitumor activity in vitro and in vivo, it has not been clinically used because of its low therapeutic efficacy and severe toxicity. Among CPT analogues, irinotecan hydrochloride (CPT-11) has recently been shown to be active against colorectal, lung, and ovarian cancer. CPT-11 itself is a prodrug and is converted to 7-ethyl-10-hydroxy-CPT (known as SN-38), a biologically active metabolite of CPT-11, by carboxylesterases in vivo. A number of camptothecin derivatives are in development, the structures of which are shown below.

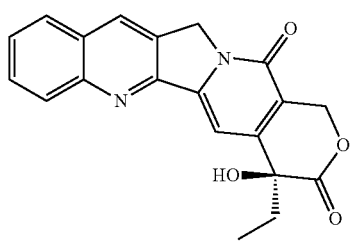

Camptothecin

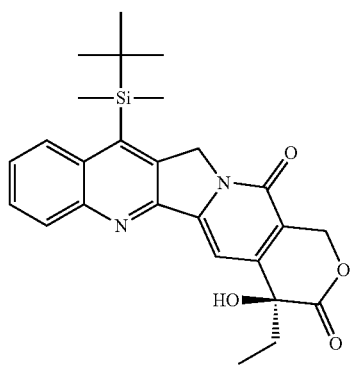

Silatecan

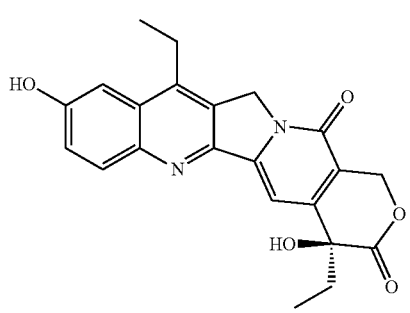

SN-38

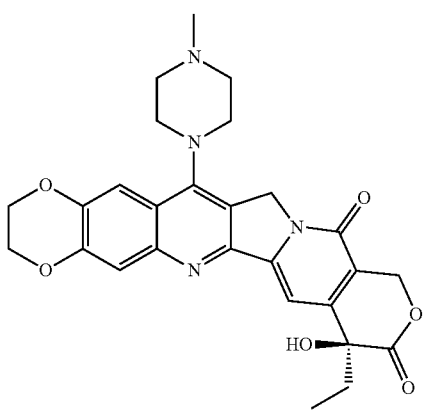

Lurtotecan

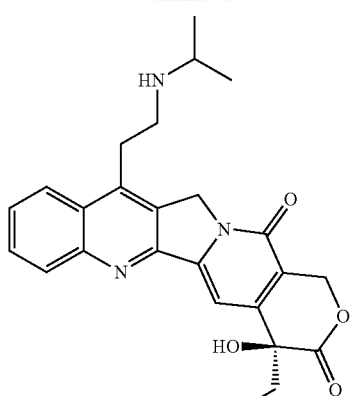

CKD 602

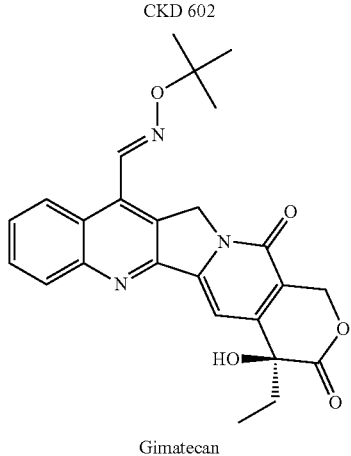

Gimatecan

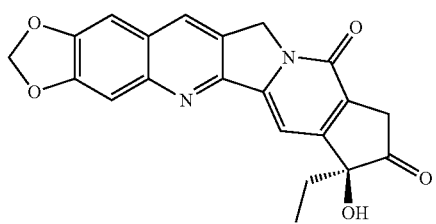

S38809

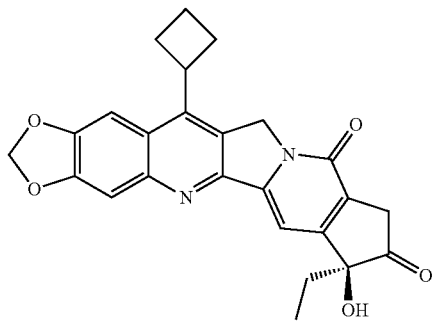

S39625

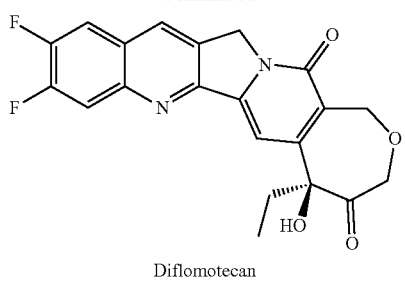

Diflomotecan

Several anthracycline derivates have been produced and have found use in the clinic for the treatment of leukemias, Hodgkin's lymphoma, as well as cancers of the bladder, breast, stomach, lung, ovaries, thyroid, and soft tissue sarcoma. Such anthracycline derivatives include daunorubicin (also known as Daunomycin or daunomycin cerubidine), doxorubicin (also known as DOX, hydroxydaunorubicin, or adriamycin), epirubicin (also known as Ellence or Pharmorubicin), idarubicin (also known as 4-demethoxydaunorubicin, Zavedos, or Idamycin), and valrubicin (also known as N-trifluoroacetyladriamycin-14-valerate or Valstar).

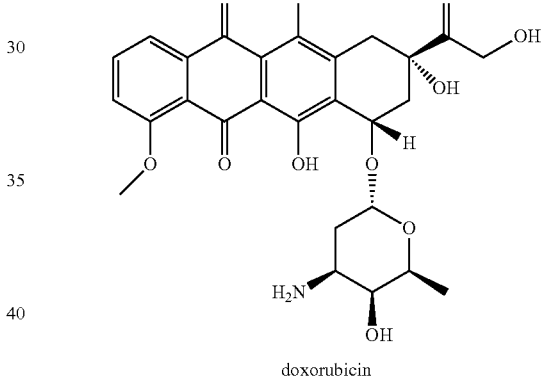

doxorubicin

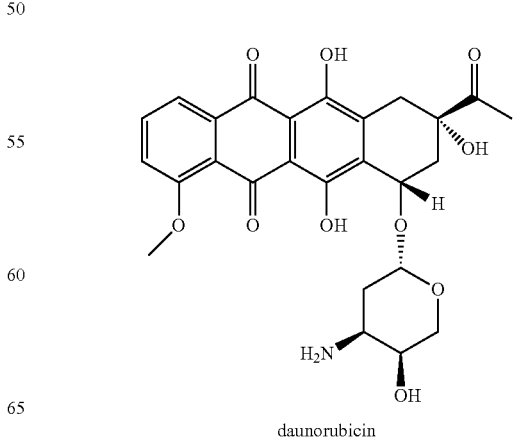

daunorubicin

-continued

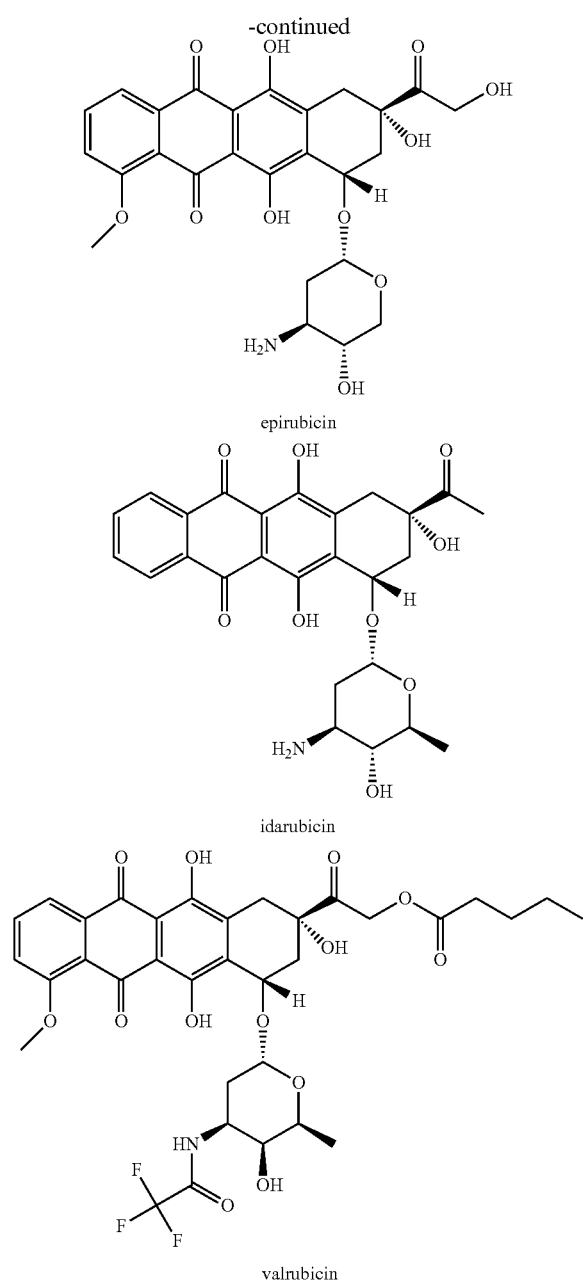

epirubicin idarubicin valrubicin

Platinum based therapeutics are well known in the literature. Platinum therapeutics are widely used in oncology and act to crosslink DNA which results in cell death (apoptosis). Carboplatin, picoplatin, cisplatin, and oxaliplatin are exemplary platinum therapeutics and the structures are shown below.

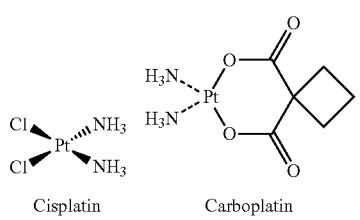

Cisplatin      Carboplatin

-continued

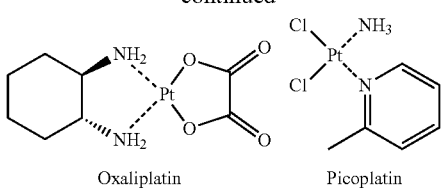

Oxaliplatin      Picoplatin

Additional molecularly targeted therapeutics are also in development. Examples include E7016, XL765, TG101348, E7820, eribulin, INK 128, TAK-385, MLN2480, TAK733, MLN-4924, motesanib, ixazomib, TAK-700, dacomitinib, and sunitinib. The structures of each are shown below.

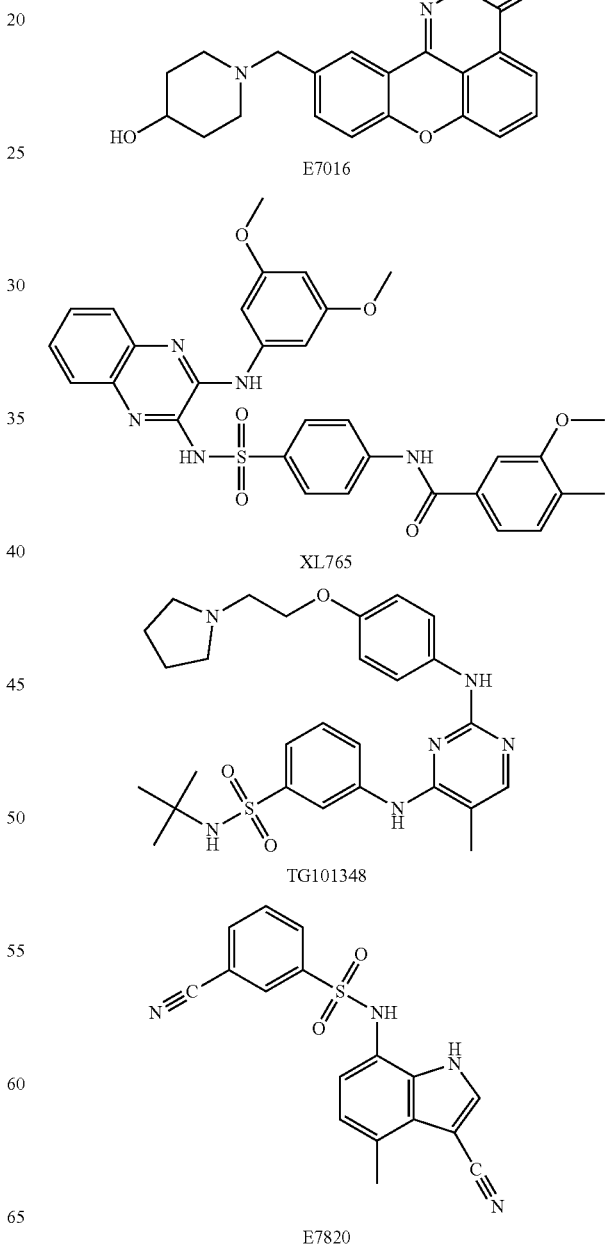

E7016

XL765

TG101348

E7820

15
-continued
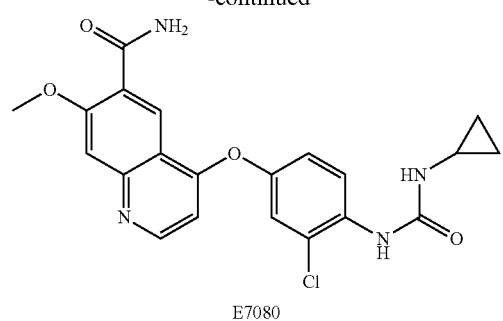
E7080
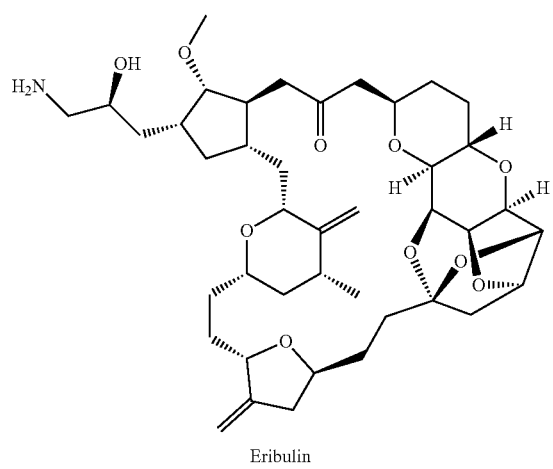
Eribulin
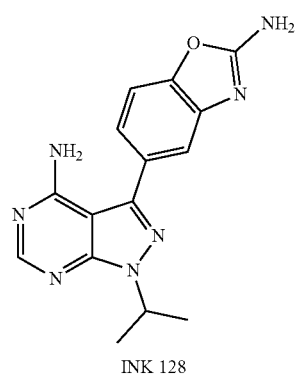
INK 128
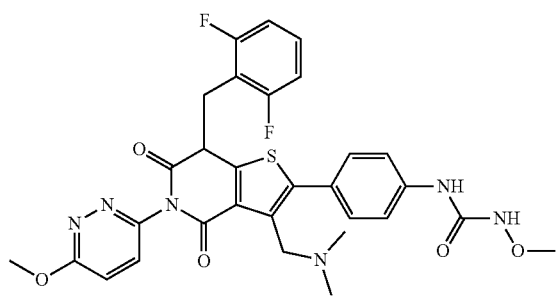
TAK-385
16
-continued
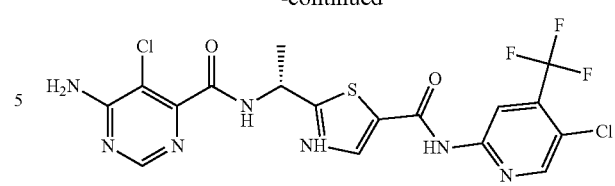
MLN2480
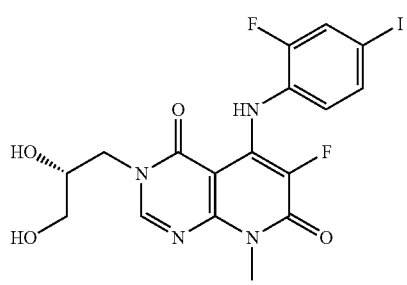
TAK-733
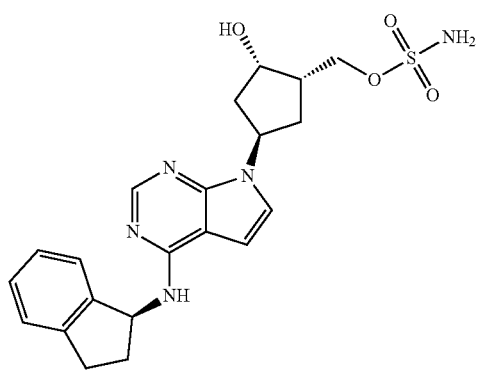
MLN-4924
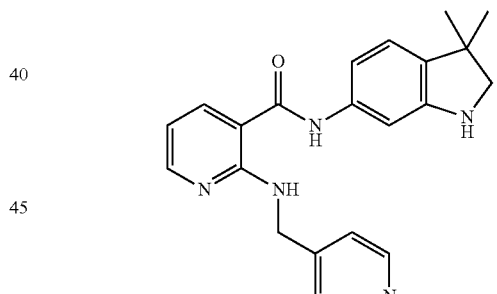
Motesanib
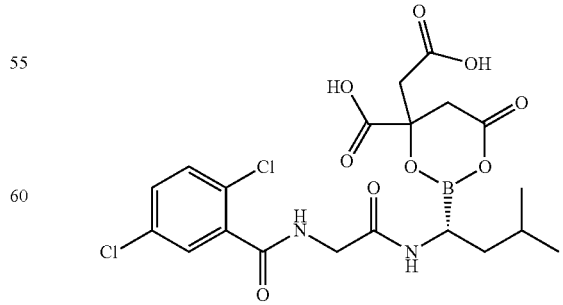
Ixazomib 17
-continued
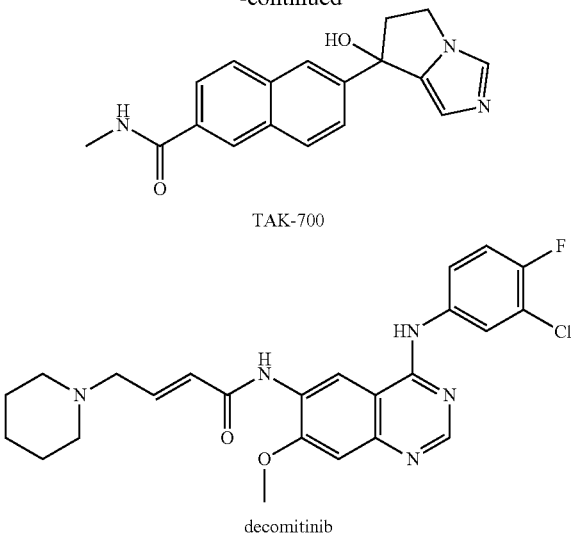
TAK-700
decomitinib
18
-continued
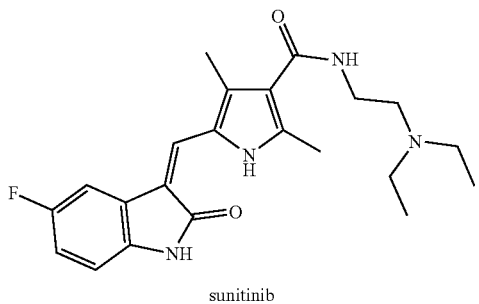 [SMILES: CCN(CC)CCNC(=O)c1c(C)[nH]c(/C=C2\C(=O)Nc3ccc(F)cc32)c1C]
sunitinib
Further examples of molecularly targeted therapeutics include crizotinib, axitinib, PF 03084014, PD 0325901, PF 05212384, PF 04449913, ridaforlimus, MK-1775, MK-2206, GSK2636771, GSK525762, eltrombopag, dabrefenib, and foretinib. The structures of each are shown below.
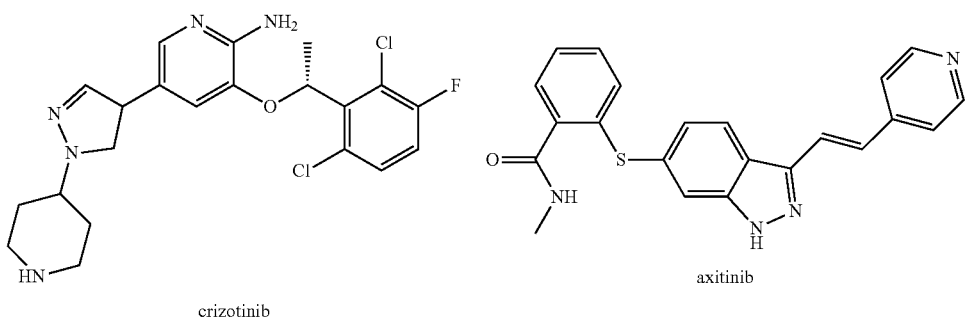
crizotinib
axitinib
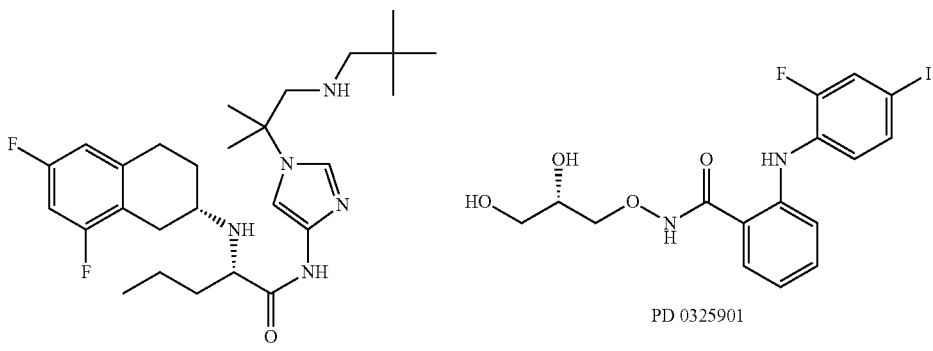
PF 03084014
PD 0325901

-continued
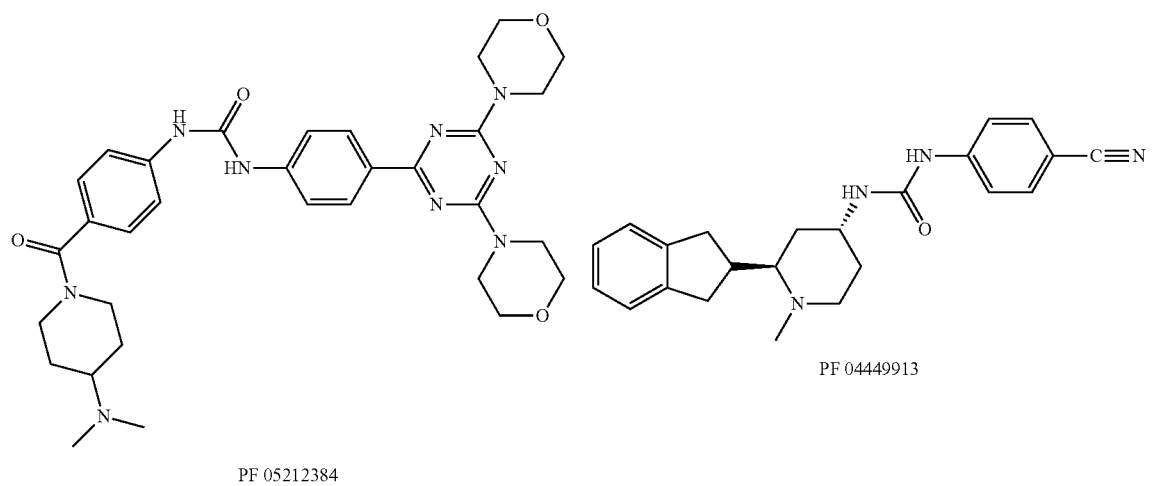
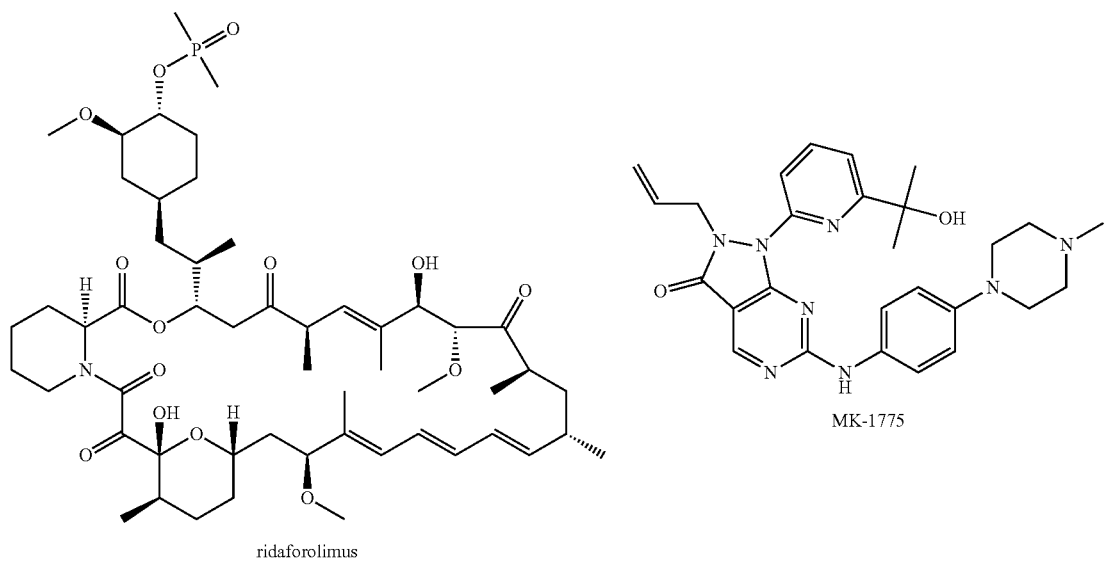
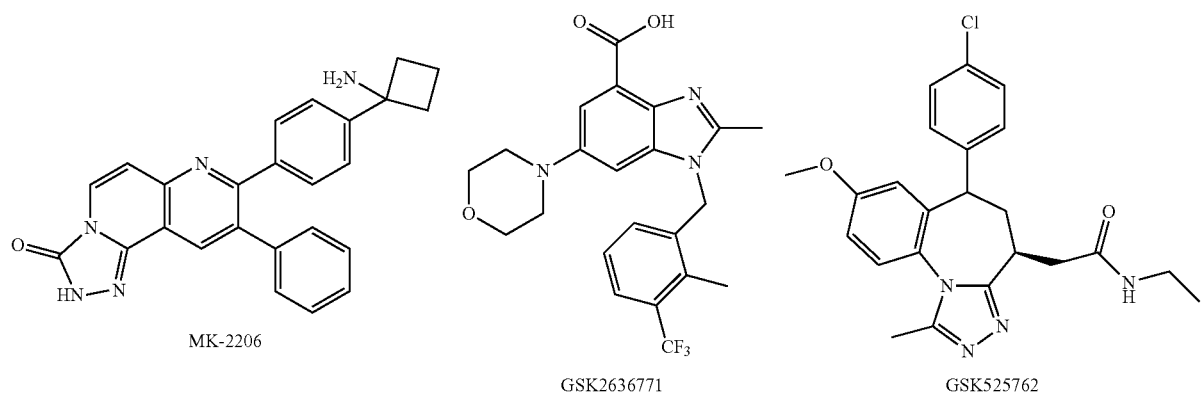

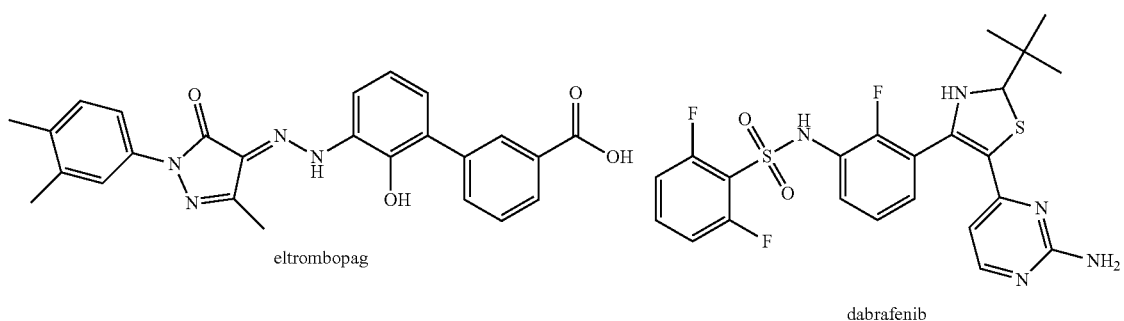
eltrombopag
dabrafenib
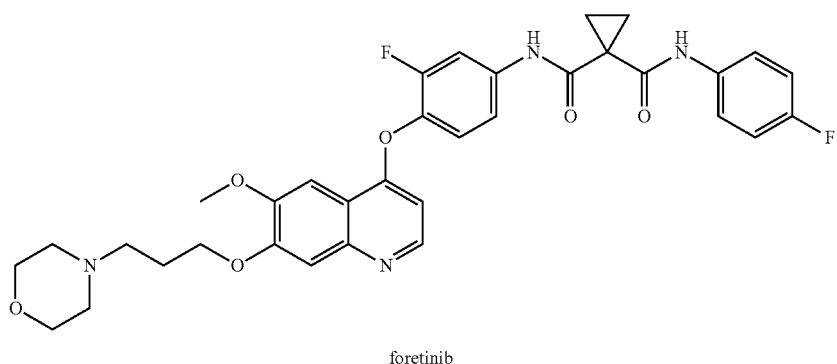
foretinib
Yet further examples of molecularly targeted therapeutics include lapatinib, pazopanib, CH5132799, RO4987655, RG7338, A0379, erlotinib, pictilisib, GDC-0032, venurafenib, GDC-0980, GDC-0068, arry-520, pasireotide, dovitinib, and cobmetinib. The structures of each are shown below.
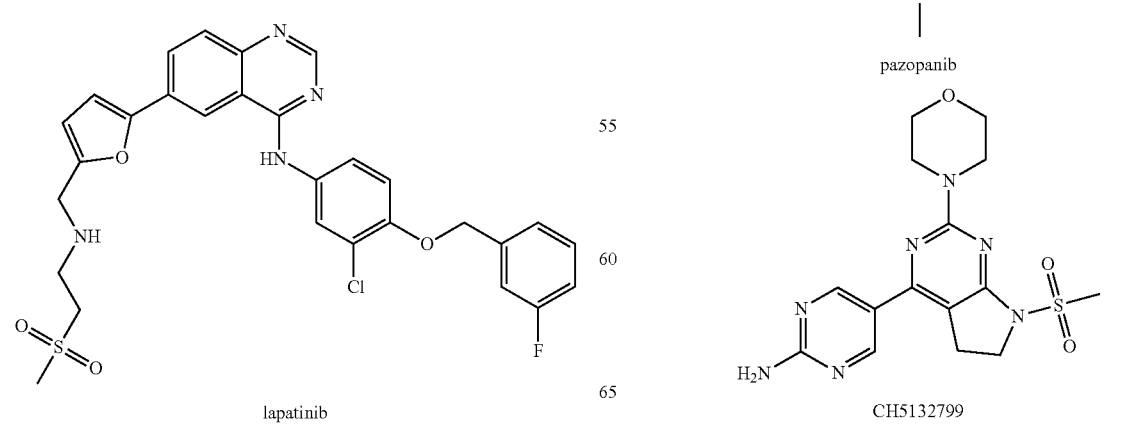
lapatinib
pazopanib
CH5132799

23
-continued
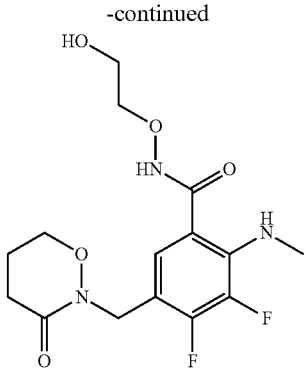
RO4987655
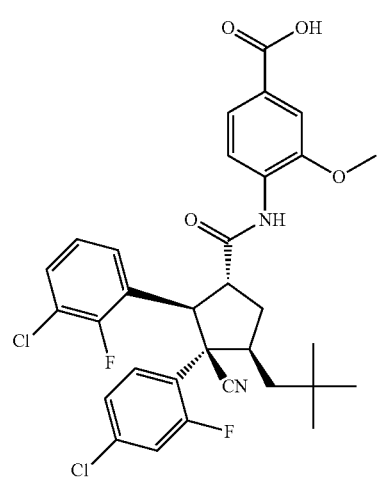
RG7388
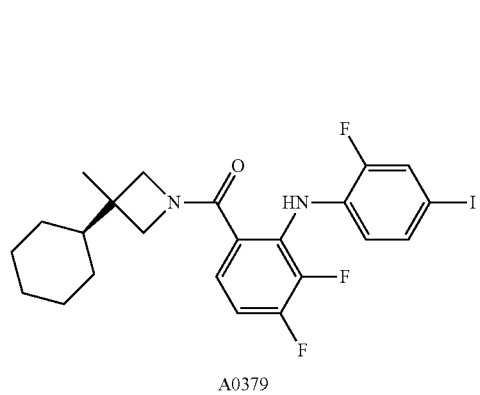
A0379
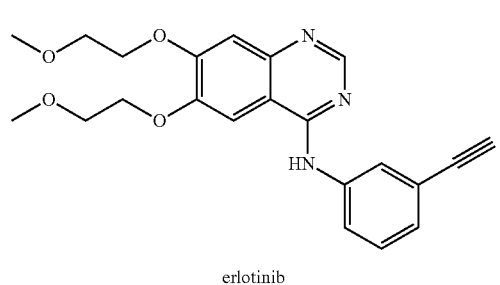
erlotinib
24
-continued
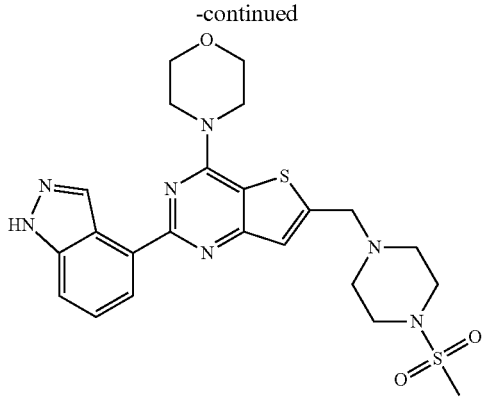
pictilisib
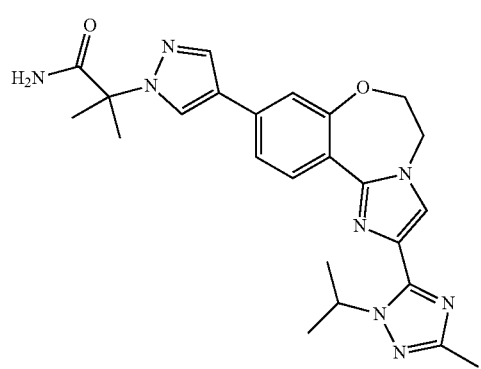
GDC-0032
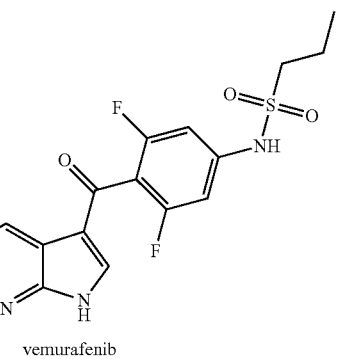
vemurafenib
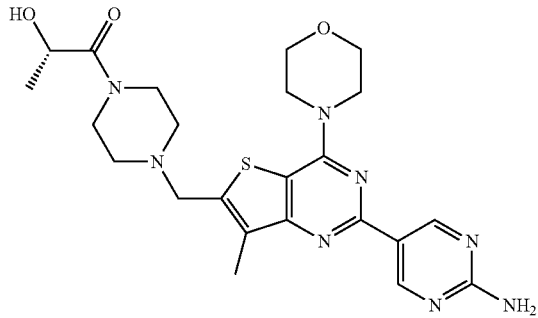
GDC-0980

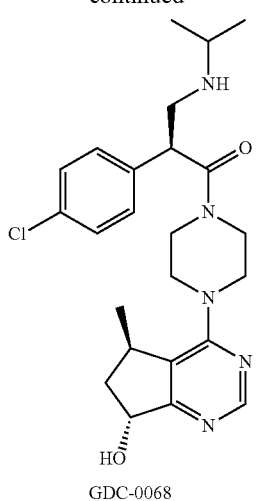
GDC-0068
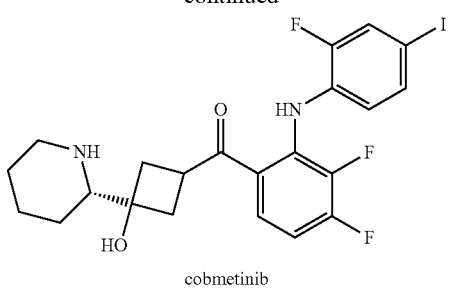
cobmetinib
Additional examples of molecularly targeted therapeutics include buparlisib, AVL-292, romidepsin, arry-797, lenalidomide, thalidomide, apremilast, AMG-900, AMG208, rucaparib, NVP-BEZ 235, AUY922, LDE225, and midostaurin. The structures of each are shown below.
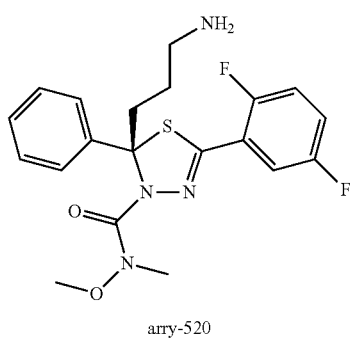
arry-520
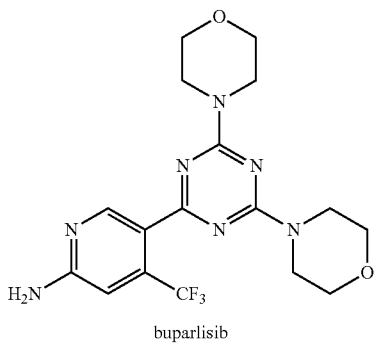
buparlisib
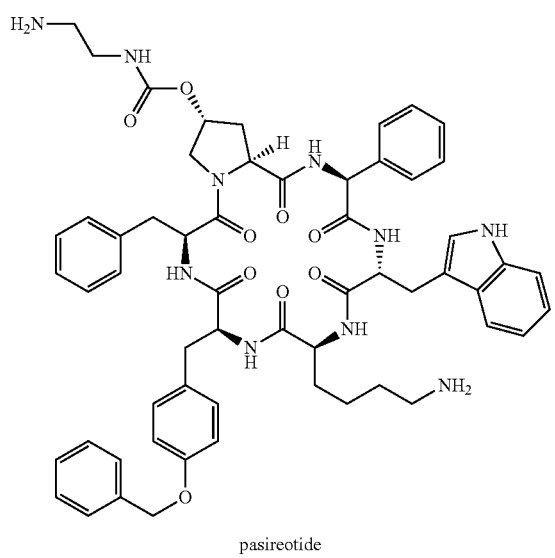
pasireotide
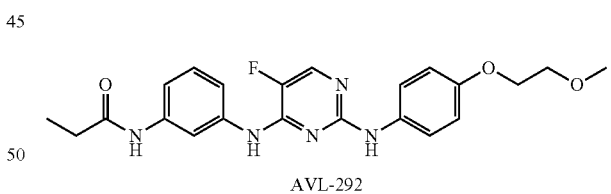
AVL-292
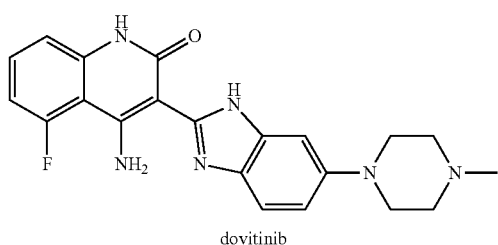
dovitinib
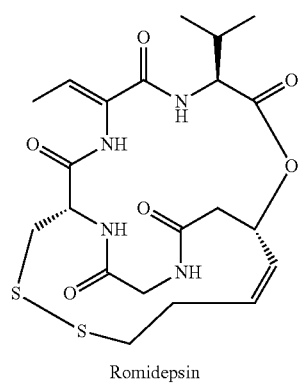
Romidepsin

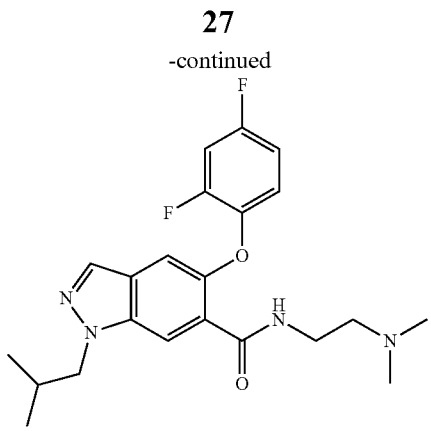
arry-797
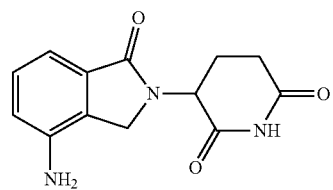
Lenalidomide
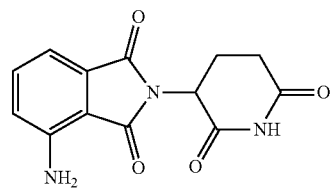
Thalidomide
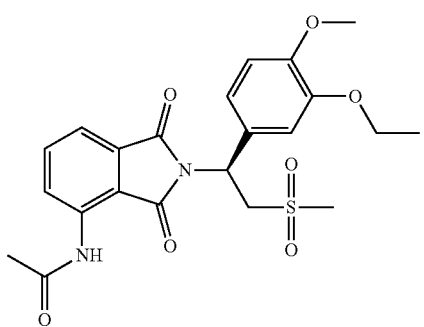
Apremilast
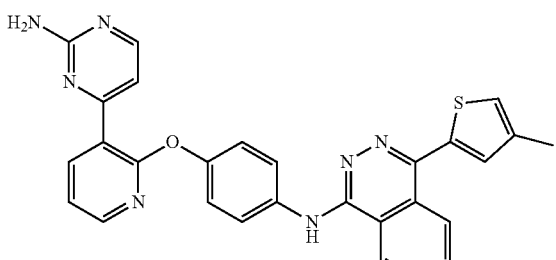
AMG-900
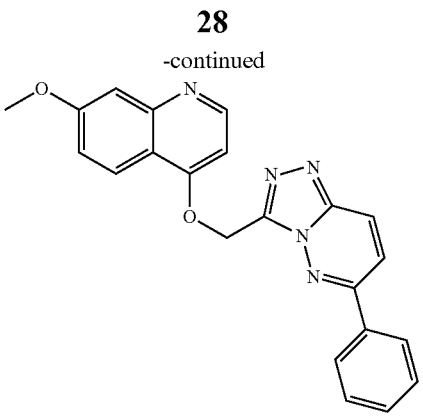
AMG208
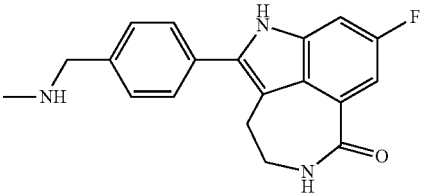
Rucaparib
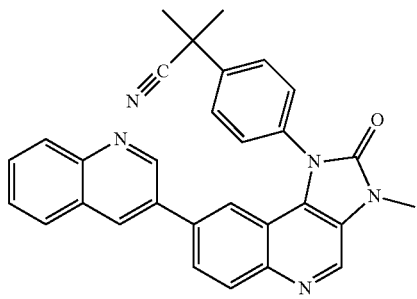
NVP-BEZ 235
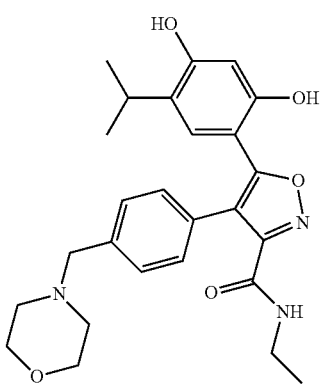
AUY922
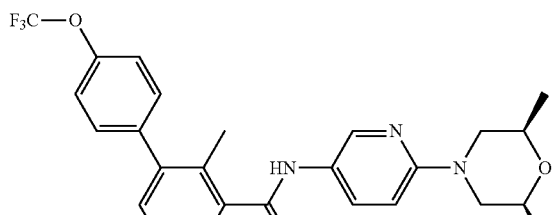
LDE225

-continued

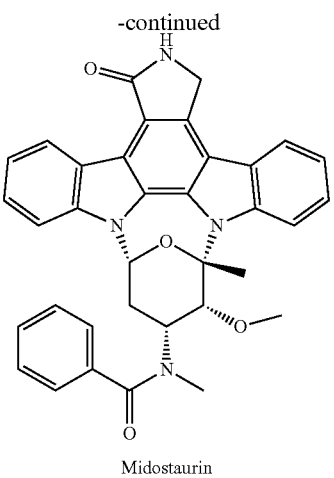

Midostaurin

3. Description of Exemplary Embodiments

The present invention provides a method for treating cancer in a patient in need thereof comprising administering IT-139, or a pharmaceutically acceptable composition thereof, in combination with a chemotherapeutic agent or an immuno-oncology agent.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering IT-139, or a pharmaceutically acceptable composition thereof, in combination with a chemotherapeutic agent or an immuno-oncology agent.

Another embodiment provides a method for treating cancer by reducing the amount of GRP78 in cancer cells following administration of IT-139.

According to another embodiment, the present invention provides a method for treating cancer by reducing the amount of GRP78 in cancer cells following administration of IT-139 in combination with a chemotherapy agent or an immune-oncology agent, wherein the administration of IT-139, or a pharmaceutically acceptable composition thereof, results in a reduction in the amount of GRP78 as compared to administration of the chemotherapy agent or immune-oncology agent alone.

The order of administration of therapeutics should be carefully considered. Without wishing to be bound to any particular theory, the mechanism of action and down-regulation of GRP78 dictates that any chemotherapeutic agent should be administered first, followed by IT-139 for maximum therapeutic benefit. As stated above, treatment with a range of chemotherapeutic agents results in an increase ER stress, which induces production of GRP78. This process is a cellular survival mechanism. Administration of IT-139 decreases the level of stress-induced GRP78, which removes a cellular survival pathway. The ultimate result is increased cancer cell death and increased anti-tumor effect.

According to one embodiment of the present invention provides a method for treating cancer in a patient in need thereof, comprising the steps of:
1) administering to the patient a chemotherapy agent;
2) subsequently administering IT-139, or a pharmaceutically acceptable composition thereof; to the patient; and
3) optionally repeating steps 1 and 2.

In certain embodiments, the IT-139, or a pharmaceutically acceptable composition thereof, is administered 1 day after the chemotherapy agent. In other embodiments, IT-139, or a pharmaceutically acceptable composition thereof, is administered to the patient 1 week after the chemotherapy agent. In yet other embodiments, IT-139 is administered to a patient between 1 and seven days after the chemotherapy agent.

In certain embodiments, the IT-139, or a pharmaceutically acceptable composition thereof, is administered simultaneously with the chemotherapy agent. In certain embodiments, the IT-139, or a pharmaceutically acceptable composition thereof, and the chemotherapy agent are administered within about 20-28 hours of each other, or within about 22-26 hours of each other, or within about 24 hours of each other.

In certain embodiments, the IT-139, or a pharmaceutically acceptable composition thereof, is administered before the chemotherapy agent. In certain embodiments, the IT-139, or a pharmaceutically acceptable composition thereof, is administered at least about 8-16 hours before the chemotherapy agent, or at least about 10-14 hours before the chemotherapy agent, or at least about 12 hours before the chemotherapy agent.

In certain embodiments, the IT-139, or a pharmaceutically acceptable composition thereof, is administered at least about 20-28 hours before the chemotherapy agent, or at least about 22-26 hours before the chemotherapy agent, or at least about 24 hours before the chemotherapy agent.

In certain embodiments, the IT-139, or a pharmaceutically acceptable composition thereof, is administered at least about 44-52 hours before the chemotherapy agent, or at least about 46-50 hours before the chemotherapy agent, or at least about 48 hours before the chemotherapy agent.

In certain embodiments, the IT-139, or a pharmaceutically acceptable composition thereof, is administered at least about 64-80 hours before the chemotherapy agent, or at least about 70-74 hours before the chemotherapy agent, or at least about 72 hours before the chemotherapy agent.

In certain embodiments, the IT-139, or a pharmaceutically acceptable composition thereof, is administered before the chemotherapy agent. In certain embodiments, the IT-139, or a pharmaceutically acceptable composition thereof, is administered at least about 8-16 hours after the chemotherapy agent, or at least about 10-14 hours after the chemotherapy agent, or at least about 12 hours after the chemotherapy agent.

In certain embodiments, the IT-139, or a pharmaceutically acceptable composition thereof, is administered at least about 20-28 hours after the chemotherapy agent, or at least about 22-26 hours after the chemotherapy agent, or at least about 24 hours after the chemotherapy agent.

In certain embodiments, the IT-139, or a pharmaceutically acceptable composition thereof, is administered at least about 44-52 hours after the chemotherapy agent, or at least about 46-50 hours after the chemotherapy agent, or at least about 48 hours after the chemotherapy agent.

In certain embodiments, the IT-139, or a pharmaceutically acceptable composition thereof, is administered at least about 64-80 hours after the chemotherapy agent, or at least about 70-74 hours after the chemotherapy agent, or at least about 72 hours after the chemotherapy agent.

In certain embodiments, the chemotherapeutic agent is selected from the group consisting of gemcitabine, nanoparticle albumin paclitaxel, paclitaxel, docetaxel, cabazitaxel, oxaliplatin, cisplatin, carboplatin, doxorubicin, daunorubicin, sorafenib, everolimus and vemurafenib. In certain embodiments, the chemotherapeutic agent is gemcitabine.

According to one embodiment of the present invention provides a method for treating pancreatic cancer in a patient in need thereof, comprising the steps of:
1) administering a gemcitabine and albumin nanoparticle paclitaxel;
2) subsequently administering IT-139, or a pharmaceutically acceptable composition thereof; and
3) optionally repeating steps 1 and 2.

In certain embodiments, the IT-139, or a pharmaceutically acceptable composition thereof, is administered simultaneously with gemcitabine. In certain embodiments, the IT-139, or a pharmaceutically acceptable composition thereof, and gemcitabine are administered within about 20-28 hours of each other, or within about 22-26 hours of each other, or within about 24 hours of each other.

In certain embodiments, the IT-139, or a pharmaceutically acceptable composition thereof, is administered before gemcitabine. In certain embodiments, the IT-139, or a pharmaceutically acceptable composition thereof, is administered at least about 8-16 hours before gemcitabine, or at least about 10-14 hours before gemcitabine, or at least about 12 hours before gemcitabine.

In certain embodiments, the IT-139, or a pharmaceutically acceptable composition thereof, is administered at least about 20-28 hours before gemcitabine, or at least about 22-26 hours before gemcitabine, or at least about 24 hours before gemcitabine.

In certain embodiments, the IT-139, or a pharmaceutically acceptable composition thereof, is administered at least about 44-52 hours before gemcitabine, or at least about 46-50 hours before gemcitabine, or at least about 48 hours before gemcitabine.

According to one embodiment of the present invention provides a method for treating cancer in a patient in need thereof, comprising administering IT-139, or a pharmaceutically acceptable composition thereof, in combination with an immuno-oncology agent. In certain embodiments, the immune-oncology agent is administered to the patient prior to the administration of IT-139, or a pharmaceutically acceptable composition thereof.

In certain embodiments, the IT-139, or a pharmaceutically acceptable composition thereof, is administered simultaneously with the immuno-oncology agent. In certain embodiments, the IT-139, or a pharmaceutically acceptable composition thereof, and the immuno-oncology agent are administered within about 20-28 hours of each other, or within about 22-26 hours of each other, or within about 24 hours of each other.

In certain embodiments, the IT-139, or a pharmaceutically acceptable composition thereof, is administered before the immuno-oncology agent. In certain embodiments, the IT-139, or a pharmaceutically acceptable composition thereof, is administered at least about 8-16 hours before the immuno-oncology agent, or at least about 10-14 hours before the immuno-oncology agent, or at least about 12 hours before the immuno-oncology agent.

In certain embodiments, the IT-139, or a pharmaceutically acceptable composition thereof, is administered at least about 20-28 hours before the immuno-oncology agent, or at least about 22-26 hours before the immuno-oncology agent, or at least about 24 hours before the immuno-oncology agent.

In certain embodiments, the IT-139, or a pharmaceutically acceptable composition thereof, is administered at least about 44-52 hours before the immuno-oncology agent, or at least about 46-50 hours before the immuno-oncology agent, or at least about 48 hours before the immuno-oncology agent.

In certain embodiments, the IT-139, or a pharmaceutically acceptable composition thereof, is administered at least about 64-80 hours before the immuno-oncology agent, or at least about 70-74 hours before the immuno-oncology agent, or at least about 72 hours before the immuno-oncology agent.

In certain embodiments, the IT-139, or a pharmaceutically acceptable composition thereof, is administered after the immuno-oncology agent. In certain embodiments, the IT-139, or a pharmaceutically acceptable composition thereof, is administered at least about 8-16 hours after the immuno-oncology agent, or at least about 10-14 hours after the immuno-oncology agent, or at least about 12 hours after the immuno-oncology agent.

In certain embodiments, the IT-139, or a pharmaceutically acceptable composition thereof, is administered at least about 20-28 hours after the immuno-oncology agent, or at least about 22-26 hours after the immuno-oncology agent, or at least about 24 hours after the immuno-oncology agent.

In certain embodiments, the IT-139, or a pharmaceutically acceptable composition thereof, is administered at least about 44-52 hours after the immuno-oncology agent, or at least about 46-50 hours after the immuno-oncology agent, or at least about 48 hours after the immuno-oncology agent.

In certain embodiments, the IT-139, or a pharmaceutically acceptable composition thereof, is administered at least about 64-80 hours after the immuno-oncology agent, or at least about 70-74 hours after the immuno-oncology agent, or at least about 72 hours after the immuno-oncology agent.

In certain embodiments, the immune-oncology agent is selected from the group consisting of cytokines, checkpoint inhibitors and antibodies other than PD-1 antibodies. In certain embodiments, the immune-oncology agent is selected from the group consisting of interferon, interleukin, PD-L1 antibodies, alemtuzumab, ipilimumab, ofatumumab, atezolizumab and rituximab.

According to one embodiment of the present invention provides a method for treating cancer in a patient in need thereof, comprising administering IT-139, or a pharmaceutically acceptable composition thereof, in combination with a PD-1 antibody. In certain embodiments, the PD-1 antibody is administered prior to the administration of the IT-139, or a pharmaceutically acceptable formulation thereof.

According to one embodiment of the present invention provides a method for treating cancer in a patient in need thereof, comprising administering IT-139, or a pharmaceutically acceptable composition thereof, in combination with a PD-L1 antibody. In certain embodiments, the PD-L1 antibody is administered prior to the administration of the IT-139, or a pharmaceutically acceptable formulation thereof.

According to one embodiment of the present invention provides a method for treating cancer in a patient in need thereof, comprising administering IT-139, or a pharmaceutically acceptable composition thereof, in combination with an immuno-oncology agent other than a PD-1 antibody. In certain embodiments, the immune-oncology agent other than a PD-1 antibody is administered prior to the administration of the IT-139, or a pharmaceutically acceptable formulation thereof.

In order that the invention described herein may be more fully understood, the following examples are set forth. It will be understood that these examples are for illustrative purposes only and are not to be construed as limiting this invention in any manner.

EXEMPLIFICATION

Figure 1B:
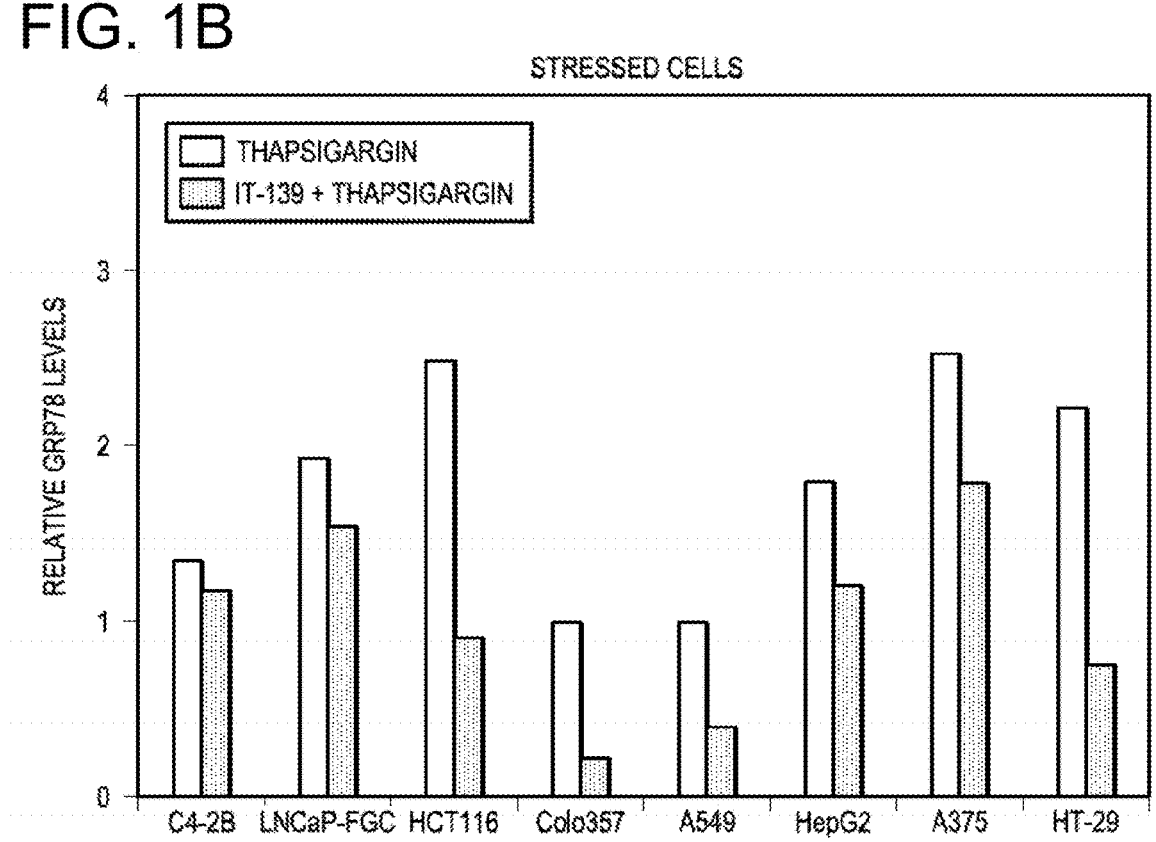

Example 1. All human primary and metastatic cell lines were maintained as described by ATCC. Cells were seeded in a 6 well plate prior to treatment with media alone (control), IT-139 (200 µM) alone, thapsigargin alone (300 nM, to induce cell stress) or IT-139 plus thapsigargin. Cell lysates were collected at 16 hours and were analyzed by western blot for anti-GRP78 antibody and normalized by GAPDH. The results shown in FIG. 1 demonstrate that IT-139 had little to no effect on unstressed cells (FIG. 1A) while treatment with IT-139 in stressed cells (IT-139 plus thapsigargin) decreased the amount of GRP78 present in stressed cells (FIG. 1B).

Figure 2A:
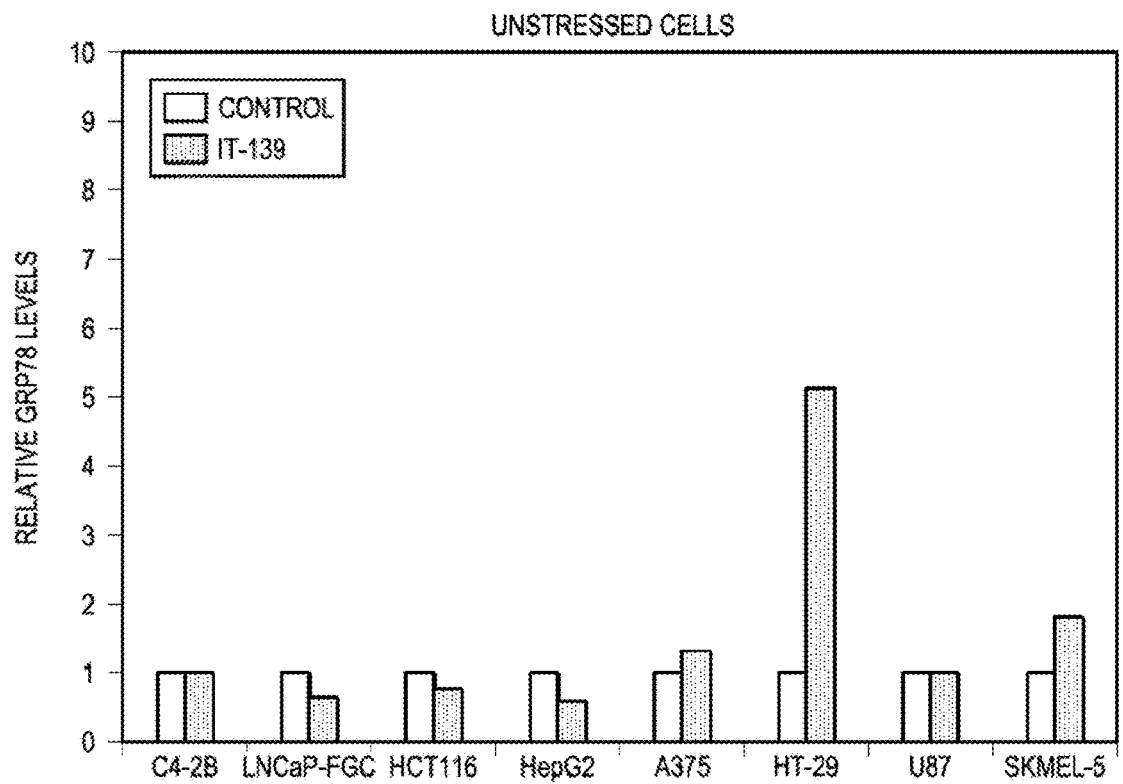
Figure 2B:
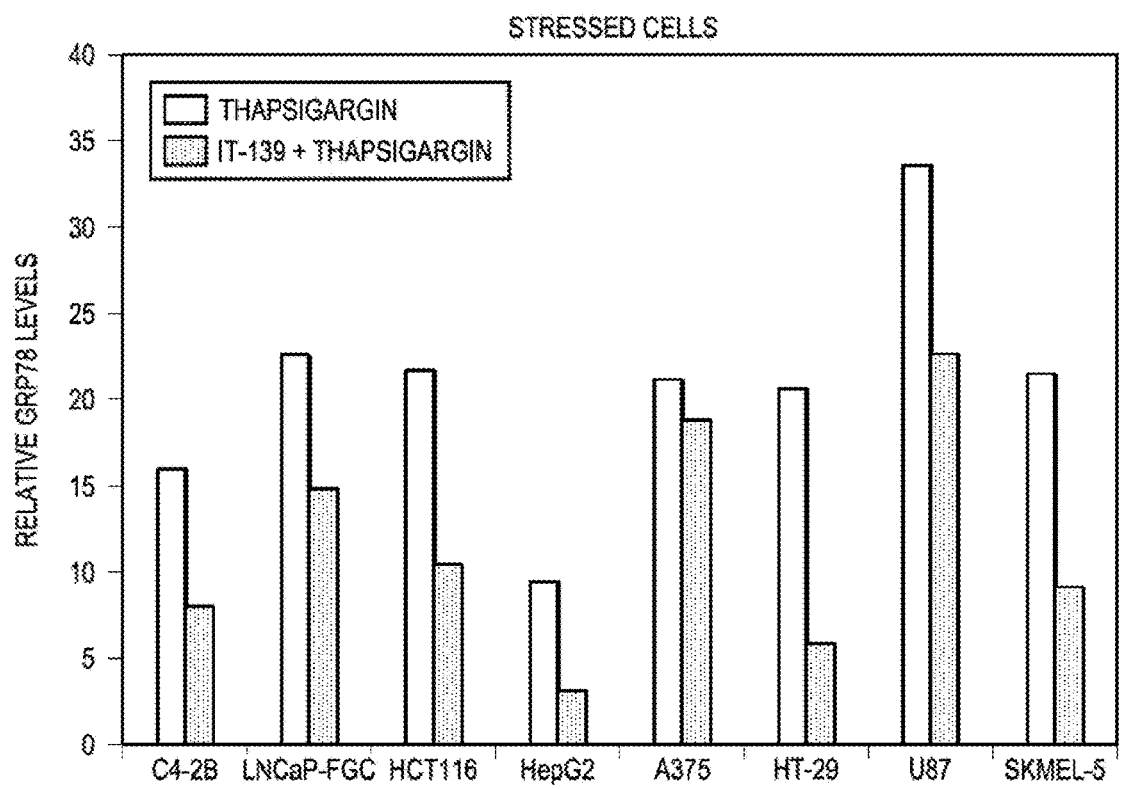

Example 2. All human primary and metastatic cell lines were maintained as described by ATCC. Cells were seeded in a 6 well plate prior to treatment with media alone (control), IT-139 (200 µM) alone, thapsigargin alone (300 nM, to induce cell stress) or IT-139 plus thapsigargin. Cell lysates were collected at 24 hours and total RNA was extracted. Quantitative real-time PCR analysis of GRP78 transcripts normalized to GAPDH. The results shown in FIG. 2 demonstrate that IT-139 treatment in unstressed cells generally has little impact on grp78 mRNA levels (FIG. 2A) while treatment with IT-139 in stressed cells (IT-139 plus thapsigargin) decreased the amount of GRP78 mRNA expression (FIG. 2B).

Figure 3:
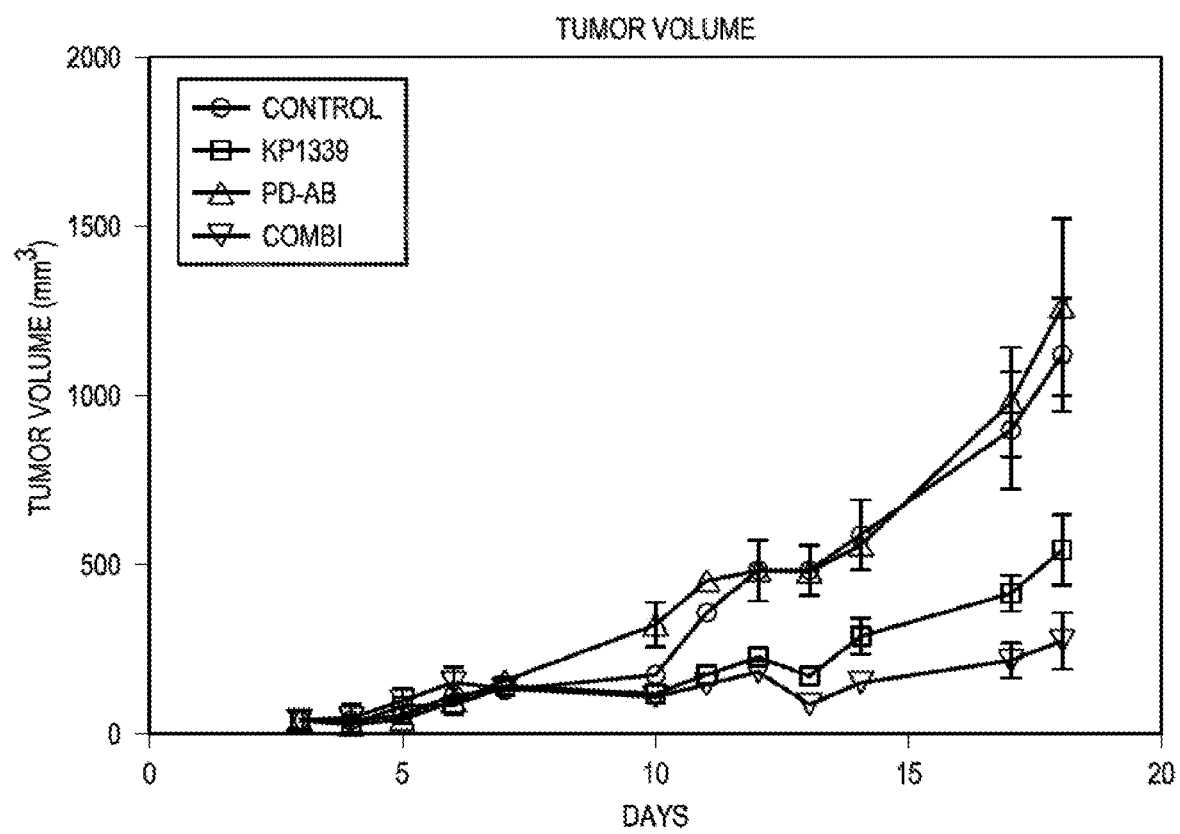
FIG. 3 depicts results from a subcutaneous syngeneic model following treatment with IT-139 and a PD-1 antibody.

Example 3. CT26 cells (1 million) were subcutaneously implanted in immunocompetent mice and allowed to grow until a palpable tumor was established (day 3). Groups of four mice per group were treated twice weekly with four total doses of either 1) saline, 2) IT-139 alone (KP1339, 30 mg/kg), 3) RPM1-14 (PD-1 antibody, 5 mg/kg), or 4) RPM1-14 and IT-139 (5 mg/kg and 30 mg/kg, respectively). IT-139 was administered intravenously and RPM1-14 was administered intraperitoneally. Administrations were made on the same day. Tumor volume was measured through day 18. Treatment with the PD-1 antibody showed no change from saline control. IT-139 demonstrated anti-tumor activity, however the combination of PD-1 antibody and IT-139 demonstrated increased antitumor activity compared to either PD-1 antibody alone or IT-139 alone. The results shown in FIG. 3 demonstrate that IT-139 increases the anti-tumor efficacy of a PD-1 antibody.

Figure 4A:
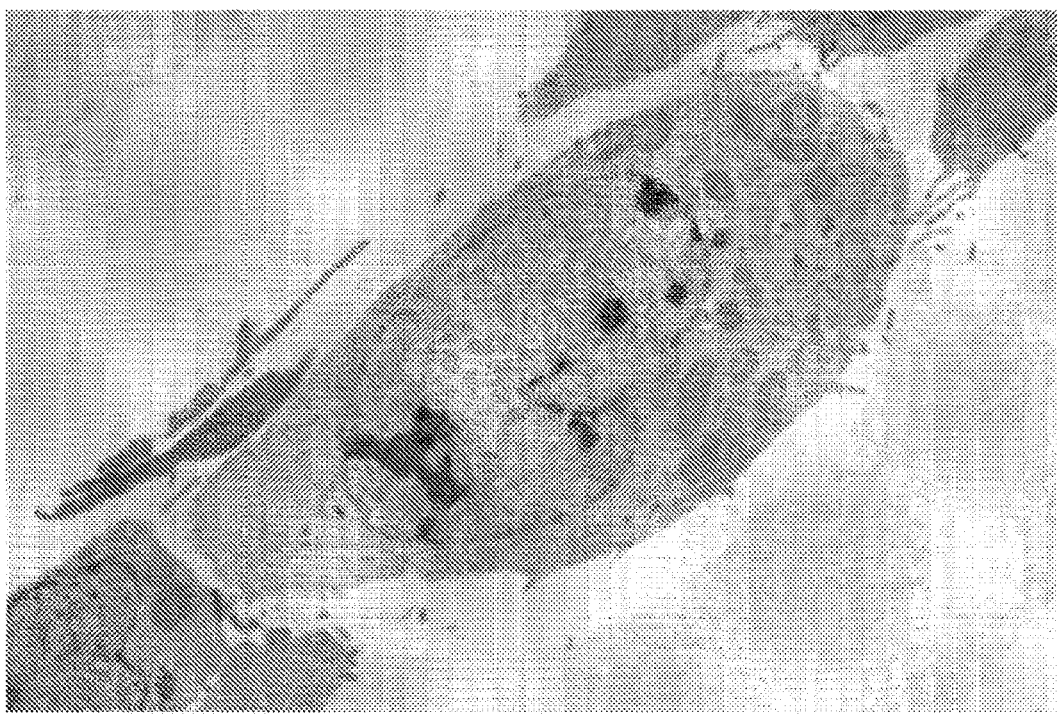
Figure 4B:
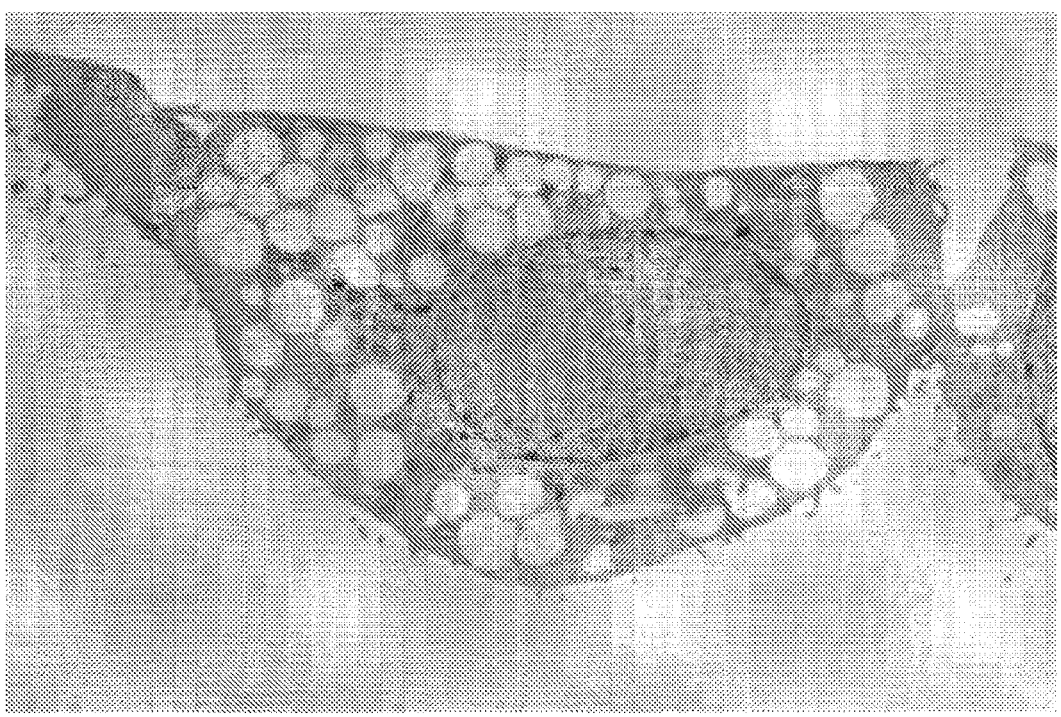

Example 4. HCT116 cell line was seeded one day prior to treatment according to ATCC guidelines. 24 hours after treatment with IT-139 (200 µM), treated and untreated cells were fixed for electron microscopic evaluation. As shown in FIG. 4, HCT116 cells treated with IT-139 (FIG. 4B) showed significant vacuolization, ER expansion and disorganization of intracellular organelles suggesting ER stress when compared to untreated cells (FIG. 4A).

Example 5. Chromatin immunoprecipitation (ChIP) assay was performed to examine Polymerase II binding to Pol II and GRP78 promoter regions in stressed and unstressed cells with IT-139 treatment. HCT116 cells were grown to 80% confluence then treated with 1.5 µg/mL tunicamycin and 200 µM IT-139 or DMSO for 16 hours. Chromatin was cross-linked using formaldehyde. Cells were harvested with trypsin and isolated nuclei were sonicated to yield fragments between 200-1000 bp. Equal amounts of chromatin were incubated with anti-Pol II antibody overnight then pulled down with Staph A cells. Cross-linking was reversed and the DNA was purified using a GeneElute PCR cleanup kit from Sigma. Purified DNA and input samples were subjected to 30 cycles of PCR with primers amplifying promoter regions of Grp78 and Pol II. The products were run on a 4% agarose gel and visualized with ethidium bromide staining. IT-139 had a minimal effect on Polymerase II binding to the Pol II promoter in non-stressed cells, but reduced this binding to 40% in Tu-stressed cells. Strikingly, IT-139 dropped Polymerase II binding to the Grp78 promoter to zero in both non-stressed and Tu-stressed cells. These results are shown in FIG. 5A-C.

Figure 6A:
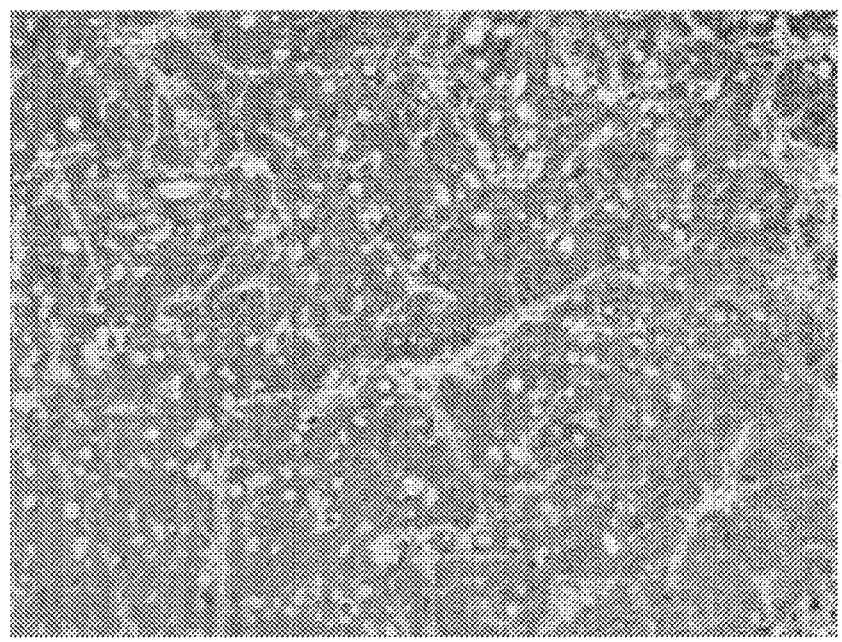
Figure 6B:
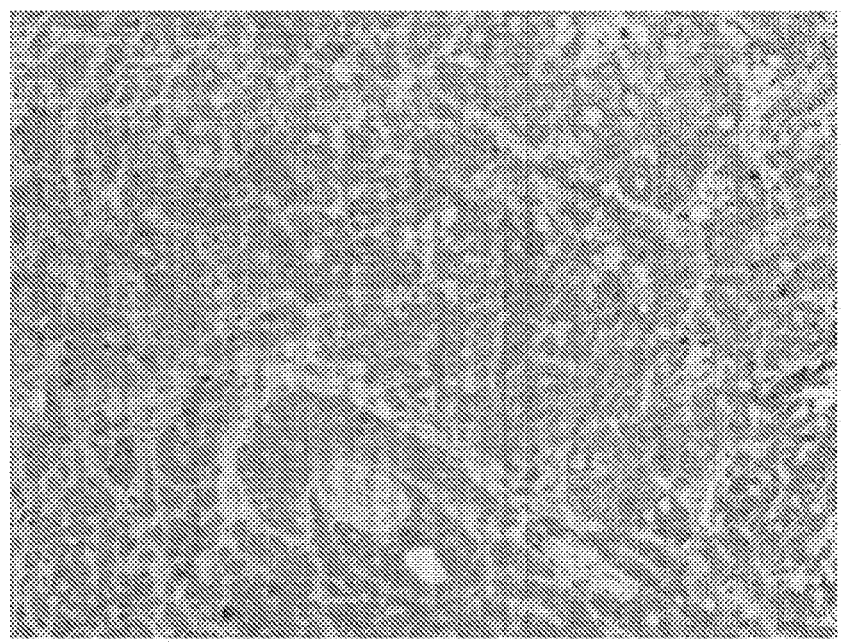

Example 6. Immunohistochemical analysis was performed to analyze the expression of GRP78 in HT-29 xenograft tumors treated with IT-139 at 30 mg/kg (q4d) in comparison to saline treated tumors. Strong immunostaining of GRP78 was observed in in saline treated tumors (FIG. 6A) in comparison to very weak staining in IT-139 treated tumors (FIG. 6B). These results indicated that IT-139 inhibits GRP78 expression in vivo.

Example 7. Normal human embryonic kidney 293T cells were either non-stressed (treated with normal media) or stressed (treated with 300 nM EndRet stress & GRP78 inducer Thapsigargin). Cell cultures were either treated with no drug (control) or 200 µM IT-139. GRP78 levels assayed by western blot; β-actin is loading control. The results are shown in FIG. 7.

Figure 8A:
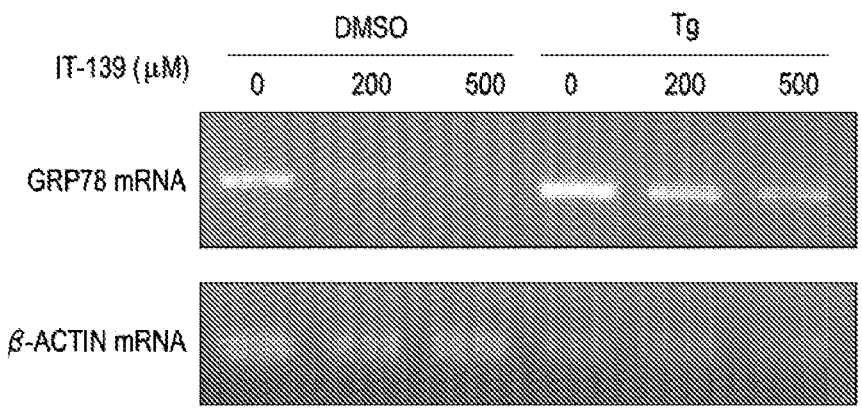
Figure 8B:
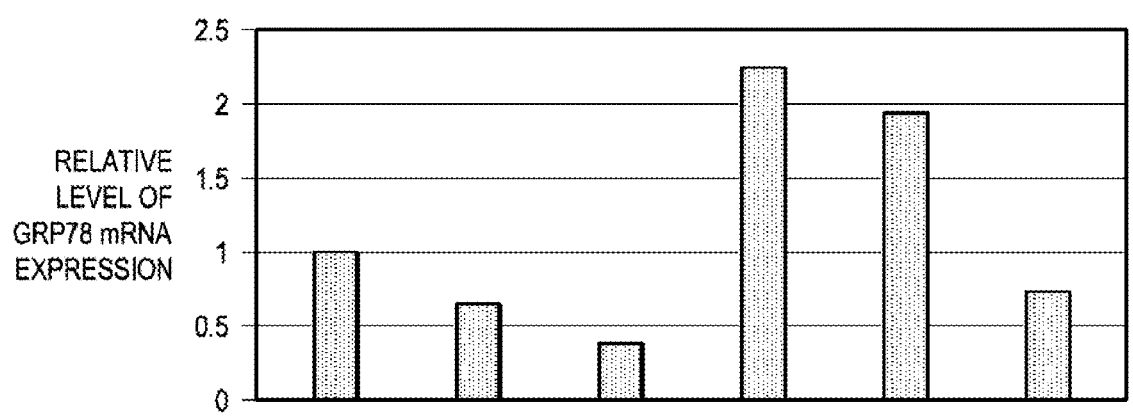

Example 8. Prostate cancer LnCaP-FGC cells were untreated (DMSO only control) or treated with 300 nM thapsigargin (Tg). Cells were co-incubated with the indicated concentrations of IT-139 and Northern blot analysis was performed on cell lysates. β-actin is the loading control. Figure shows the Northern blots. Bands were quantified and bar graph shows relative levels of GRP78 mRNA levels normalized against β-actin loading control. IT-139 suppression of GRP78 is at the transcriptional level in a dose dependent manner, as seen by Northern blot analysis of tumor cells treated with IT-139. The results are shown in FIG. 8.

Figure 9:
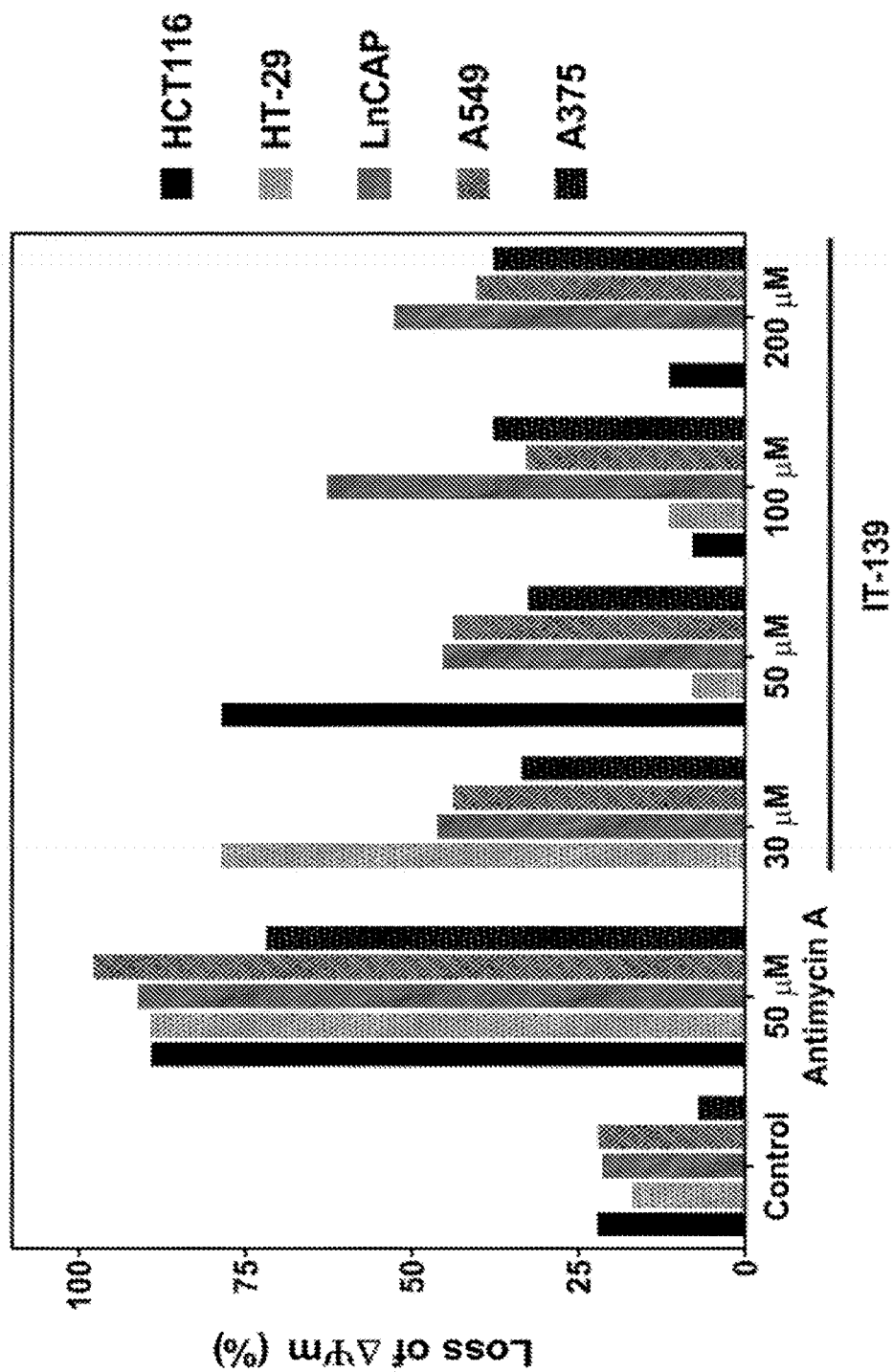
FIG. 9 depicts effects of mitochondria potential following treatment with IT-139 in multiple cell lines.

Example 9. All human primary and metastatic cell lines were maintained as described by ATCC. All cell lines (HCT116, HT-29, LNCaP, A549 and A375) were seeded in a 6 well plate 24 hours prior to treatment with IT-139 alone. All cell lines were treated with 30 uM, 50 uM, 100 uM and 200 uM with the following exceptions: treatment with 30 uM and 200 uM were omitted for HCT116 and HT29 cell lines respectively. After 24 h incubation with the drug, cells were trypsinized and re-suspended in warm PBS and stained with the JC-1 dye for 30 min at 37 C in the dark. The cells were then washed and re-suspended in warm PBS. The fluorescence of the JC-1 dye was measured by flow cytometry analysis by exciting the dye at 488 nm and detecting the JC-1 monomer through its emission at 530 nm with aggregates of JC-1 being measured at 580 nm. All cell lines treated with Antimycin A at 50 uM as positive control. Results show that both HCT116 and HT29 cell lines showed increased loss of mitochondrial potential at lower concentrations, 50 µM and 30 µM respectively, of IT-139. However, prostate (LNCaP), lung (A549) and melanoma (A375) cells showed an increase in mitochondrial depolarization at high concentrations of IT-139. Data is shown in FIG. 9.

Figure 10:
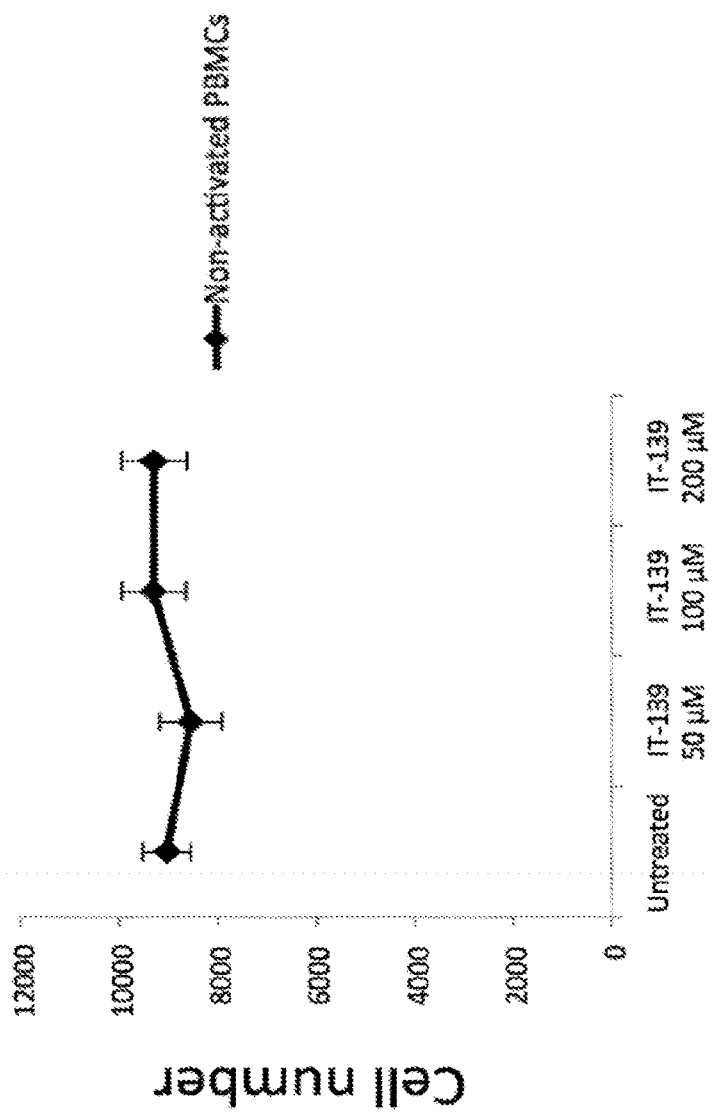
FIG. 10 depicts cell viability of normal peripheral blood mononuclear cells following treatment with IT-139.
Figure 11:
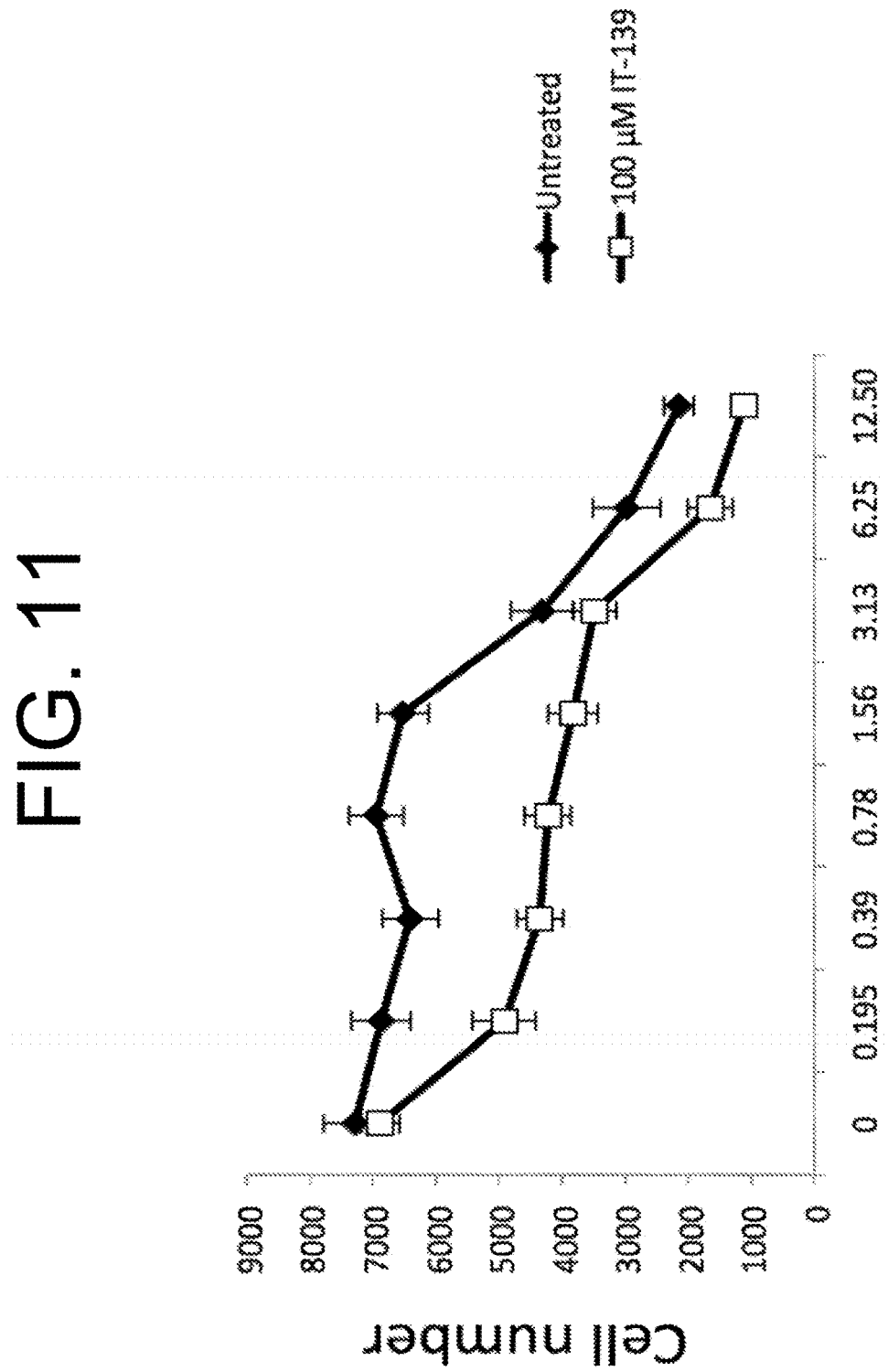
FIG. 11 depicts cell viability of normal peripheral blood mononuclear cells following treatment with IL-2 or IL-2 and IT-139.

Example 10. Prostate cancer cell line, MiaPaca2, was maintained as described by ATCC. MiaPaca2 cells co-cultured with normal peripheral blood mononuclear cells (PBMCs) treated with increasing concentrations of IT-139 (50, 100 and 200 µM) for 24 h did not show any effect upon cell viability as shown in FIG. 10. MiaPaca2 cells were either untreated or pre-treated with IT-139 (100 µM) and co-cultured with IL-2 activated PBMCs at varying doses. PBMCs were activated using 6000 IU of IL-2 for 24 h. IT-139 shows increased cell death in MiaPaca2 cells co-cultured with activated PBMCs, as shown in FIG. 11.

Figure 12:
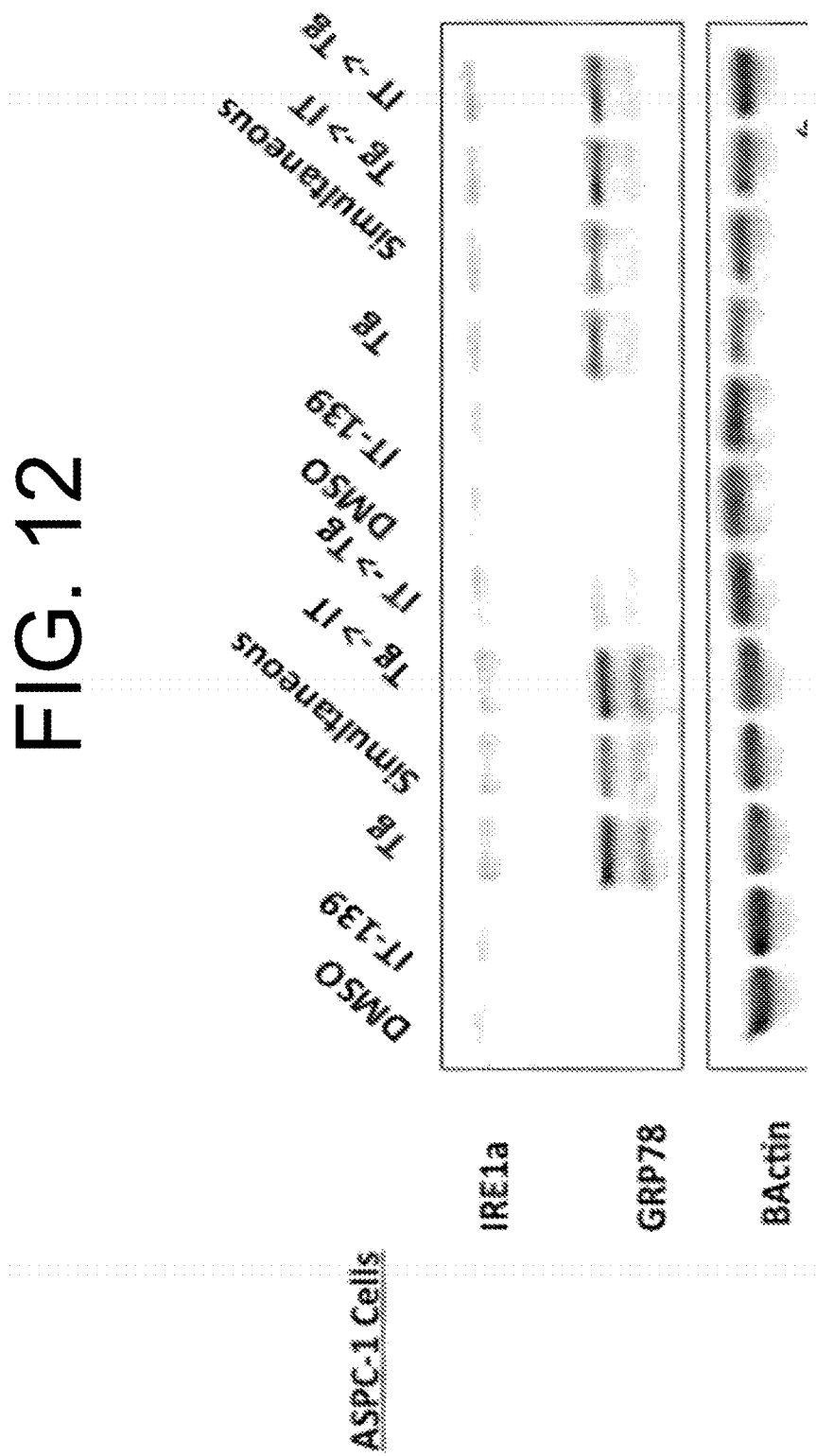
FIG. 12 depicts expression of GRP78 protein levels treated with DMSO; 150 µM IT-139; 1 µM Thapsigargin (Tg); simultaneous treatment of 150 µM IT-139 and 1 µM Tg; 1 µM Tg treated for 6 hours followed by 150 µM IT-139 for 24 hours; and 150 mM IT-139 for 24 hours followed by 1 mM Tg treatment for 24 hours for lanes 1-5, respectively. Lanes 6-12 are the same treatments incubated for a further 24 hours.
Figure 13:
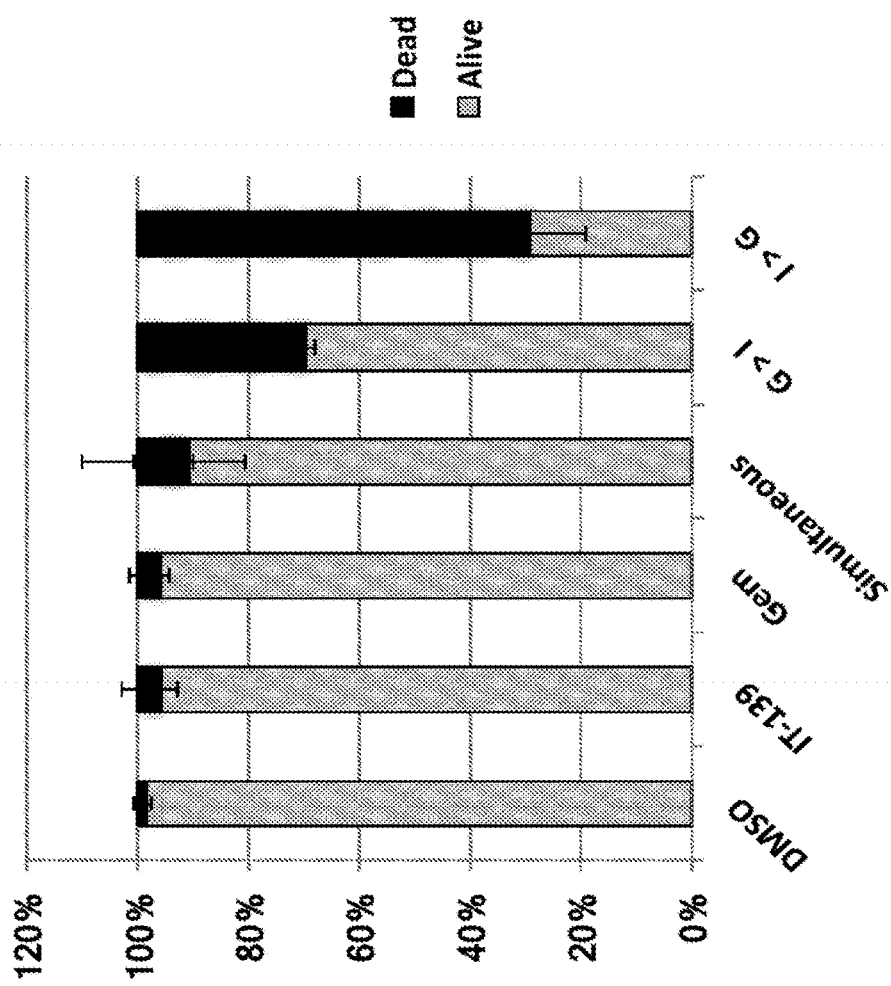
FIG. 13 depicts ASPC20 cells treated in vitro for 48 hours with DMSO (control); 150 µM IT-139; 5 µM gemcitabine; simultaneous 150 µM IT-139 and 5 µM gemcitabine; 5 µM gemcitabine for 24 hours followed by 150 µM IT-139; and 1.50 µM IT-139 followed by 24 hrs 5 gemcitabine.
Figure 14:
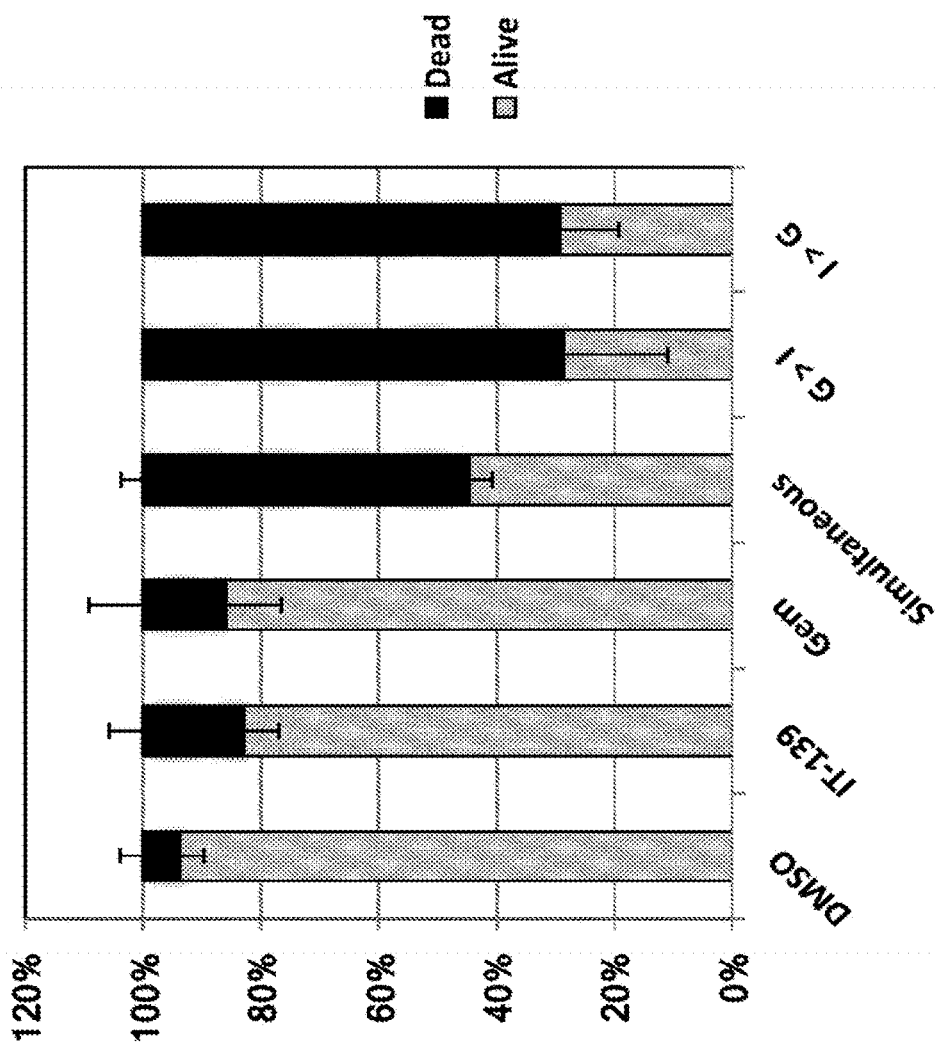
FIG. 14 depicts PANC-1 cells treated in vitro for 48 hours with DMSO (control); 150 µM IT-139; 5 µM gemcitabine; simultaneous 150 µM IT-139 and 5 µM gemcitabine; 5 µM gemcitabine for 24 hours followed by 150 µM IT-139; and 150 µM IT-139 followed by 24 hours 5 µM gemcitabine.

Example 11. Combination IT-139 and gemcitabine (GEM) treatment extend both median and overall survival in an ASPC mouse model. Likewise, combination dosing at 48 hours of Gemcitabine in combination with IT-139 in ASPC-1 cells in vitro, results in a significant change in survival when IT-139 is dosed first. In vitro ASPC20 cells are treated for 48 hours with DMSO (control), 150 µM IT-139, 5 µM gemcitabine, simultaneous 150 µM IT-139 and 5 µM gemcitabine, 5 µM gemcitabine for 24 hours followed by 150 µM IT-139, or 150 µM IT-139 followed by 24 hrs 5 µM gemcitabine. Cells are harvested and counted by trypan blue to calculate the number of dead cells versus viable cells. In ASPC20 cells, the order of dosing thapsigargin (Tg) to induce stress in combination with IT-139, affects levels of GRP78 expression at 30 hours. The results are shown in FIG. 12. In addition, the order of dosing also effects the amount of cell death, as increased cell death is observed when IT-139 is dosed before gemcitabine. The results are shown in FIG. 13. PANC-1 cells are treated in vitro for 48 hours with DMSO (control), 150 µM IT-139, 5 µM gemcitabine, simultaneous 150 µM IT-139 and 5 µM gemcitabine, 5 µM gemcitabine for 24 hours followed by 150 µM IT-139, and 150 µM IT-139 followed by 24 hours 5 µM gemcitabine DMSO (control), 150 µM IT-139, 5 µM gemcitabine, simultaneous 150 µM IT-139 and 5 µM gemcitabine, 5 µM gemcitabine for 24 hours followed by 150 µM IT-139, and 150 µM IT-139 followed by 24 hours 5 µM gemcitabine. The results are shown in FIG. 14. In PANC-1 cells, the cytotoxicity effect at 48 hours demonstrates no difference dependent on sequence of dosing of gemcitabine and IT-139.

Figure 15:
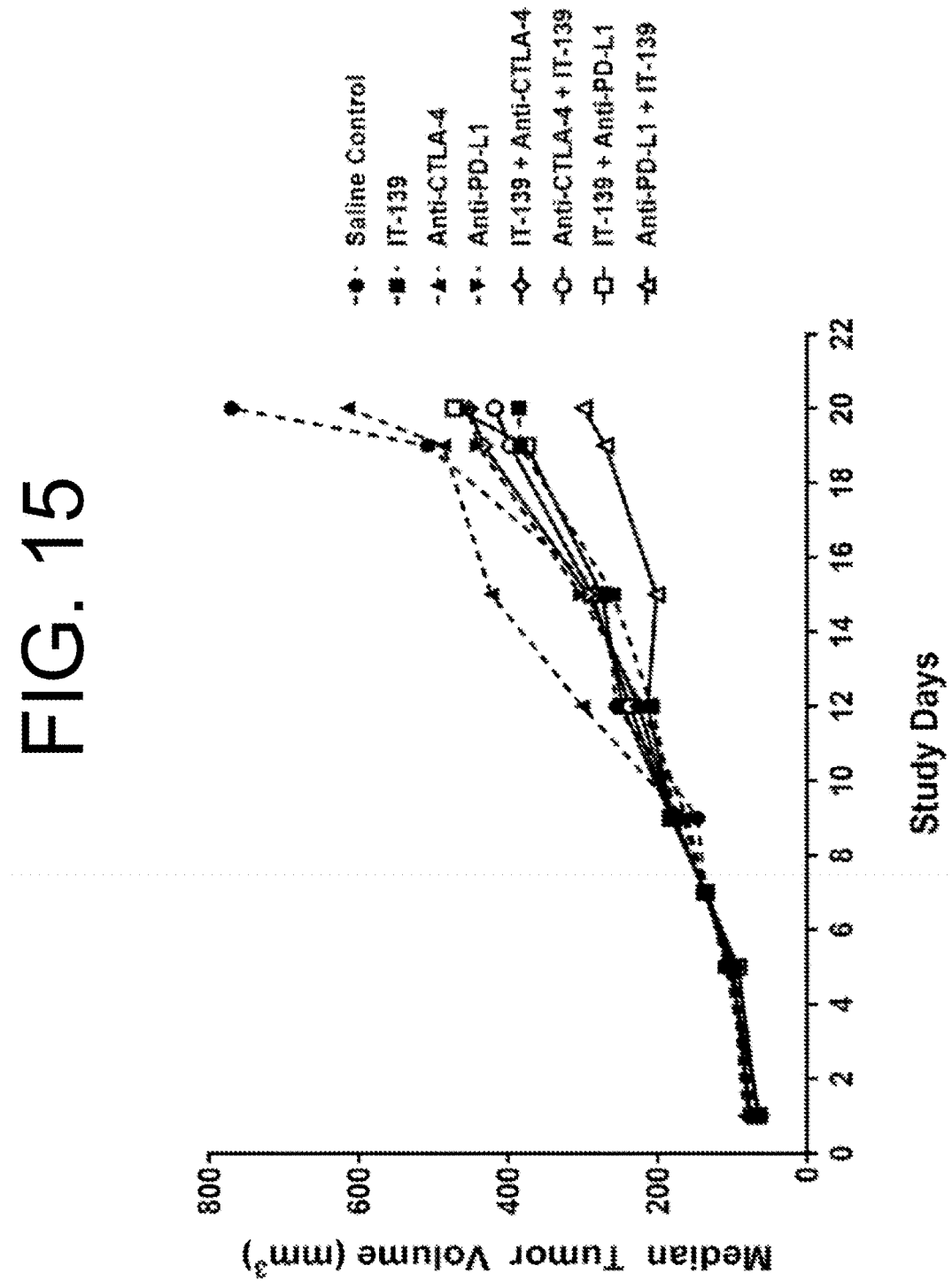
FIG. 15 depicts median tumor volume of 8 treatment groups in an A20 Mouse model
Figure 16:
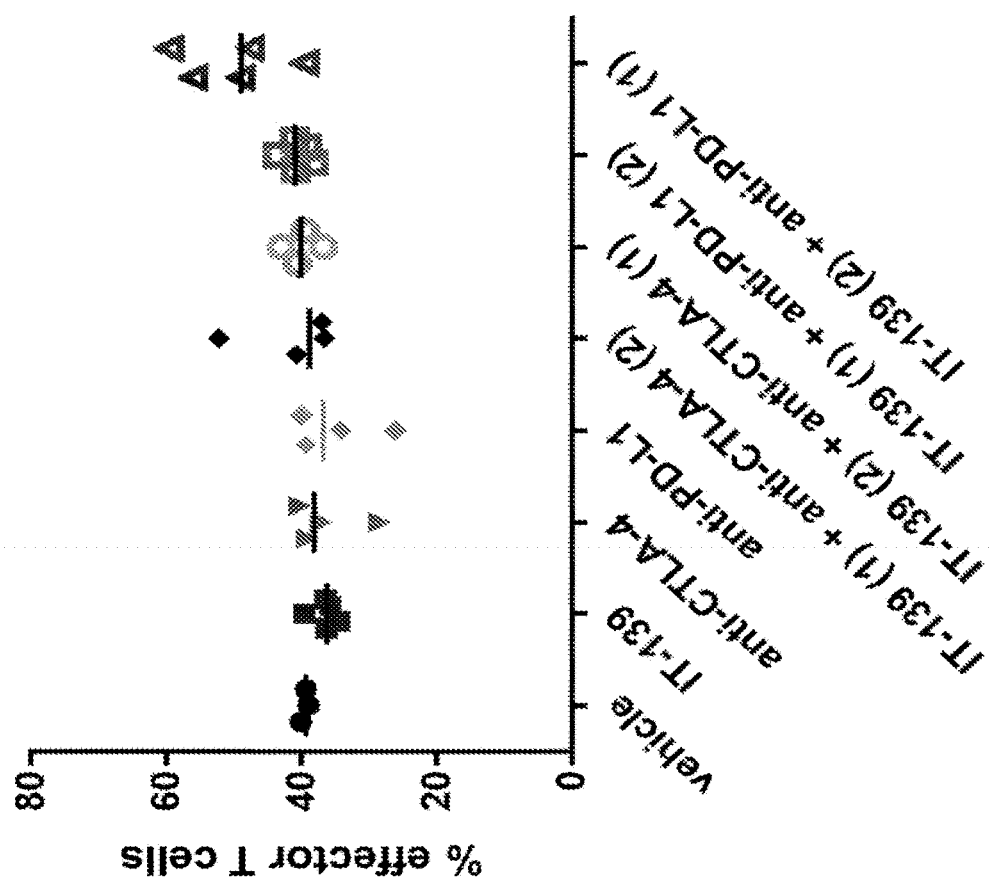
FIG. 16 depicts a scatter plot showing median % of Effector T Cells in tumor.
Figure 17:
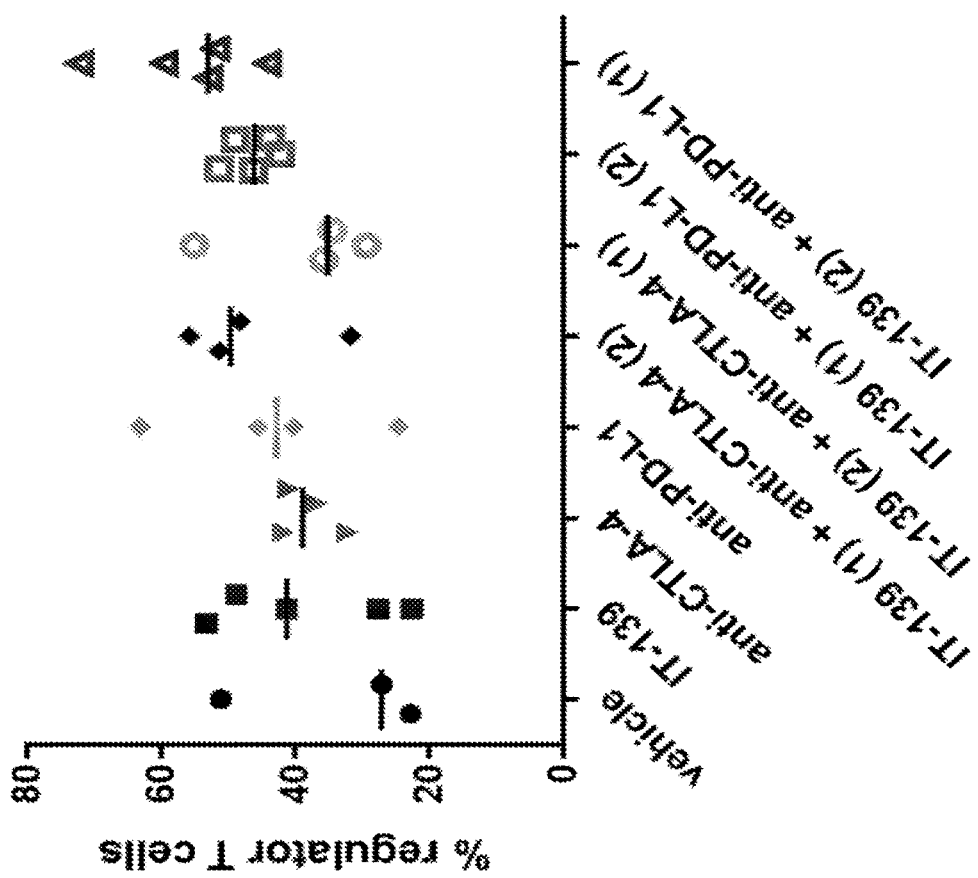
FIG. 17 depicts a scatter plot showing median % of Regulator T Cells in tumor.

Example 12. In an A20 lymphoma mouse model, 104 Balb/c mice were inoculated with lymphoma A20 cells subcutaneously on the right flank of the mice. Mice were randomized into 8 groups of 10 mice when tumors reached a mean volume of 80-120 mm$^3$. Mice were monitored daily for behavior and survival and twice weekly for body weight and tumor growth. Tumors were induced by subcutaneous injection of 5×10$^6$ of A20 cells in 200 µL RPMI 1640 medium containing matrigel (50:50, v:v, ref: 356237, BD Biosciences, France) into the right flank of hundred and four (104) Balb/C mice. The checkpoint inhibitors were Anti-PD-L1 (clone 10F.9G2; ref: Bioxcell isotype Rat IgG2b), and Anti-CTLA4 antibody (clone 9H10; ref: BE0131, bioxcell; isotype Hamster IgG1), both dosed at 10 mg/kg i.p. every 3 days. IT-139 was dosed at 30 mg/kg intravenously every 4 days. The dosage schedule is shown in Table 1 below. Average tumor volume over the course of the experiment is shown in FIG. 15. 5 tumors from each group were collected for FACS Analysis (40 tumor samples). One panel was run for Treg and T effector cells (CD45, CD3, CD4, CD8 and FoxP3), one panel for MDSCs (CD45, CD3, CD11b, Gr-1, Ly-6g, Ly-6C, Arg1, NOS2), and one panel for tumor-associated macrophages (CD54, CD11b, Gr-1, CD68, CD80, and CD206). When PD-L1 was dosed 24 hours prior to IT-139 administration there was a significant anti-tumor efficacy and a 10% increase in effector T-Cell infiltration of the tumor, shown in FIG. 16 and FIG. 17. This effect was not seen in any of the other groups. With the decrease in tumor growth in this combination group, evidence of an immunomodulatory effect with anti-PD-L1 antibody is present.

TABLE 1

A20 Immunotherapy Study Design and Grouping

| Group | No. Animals | Treatment | Dose (mg/kg/inj) | Route | Treatment schedule |
|---|---|---|---|---|---|
| 1 | 10 | Vehicle | — | IV | $D_R$, $D_{R+3}$, $D_{R+7}$, $D_{R+10}$ |
| 2 | 10 | IT-139 | 30 | IV | $D_R$, $D_{R+3}$, $D_{R+7}$, $D_{R+10}$ |
| 3 | 10 | Anti-CTLA-4 | 10 | IP | $D_{R+1}$, $D_{R+4}$, $D_{R+8}$, $D_{R+11}$ |
| 4 | 10 | Anti-PD-L1 | 10 | IP | $D_{R+1}$, $D_{R+4}$, $D_{R+8}$, $D_{R+11}$ |
| 5 | 10 | IT-139 | 30 | IV | $D_R$, $D_{R+3}$, $D_{R+7}$, $D_{R+10}$ |
|   |   | Anti-CTLA-4 | 10 | IP | $D_{R+1}$, $D_{R+4}$, $D_{R+8}$, $D_{R+11}$ |
| 6 | 10 | IT-139 | 30 | IV | $D_{R+2}$, $D_{R+5}$, $D_{R+9}$, $D_{R+12}$ |
|   |   | Anti-CTLA-4 | 10 | IP | $D_{R+1}$, $D_{R+4}$, $D_{R+8}$, $D_{R+11}$ |
| 7 | 10 | IT-139 | 30 | IV | $D_R$, $D_{R+3}$, $D_{R+7}$, $D_{R+10}$ |
|   |   | Anti-PD-L1 | 10 | IP | $D_{R+1}$, $D_{R+4}$, $D_{R+8}$, $D_{R+11}$ |
| 8 | 10 | IT-139 | 30 | IV | $D_{R+2}$, $D_{R+5}$, $D_{R+9}$, $D_{R+12}$ |
|   |   | Anti-PD-L1 | 10 | IP | $D_{R+1}$, $D_{R+4}$, $D_{R+8}$, $D_{R+11}$ |
| TOTAL | 80 |   |   |   |   |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A method for treating an adenocarcinoma in a patient in need thereof comprising administering IT-139, or a pharmaceutically acceptable composition thereof, in combination with gemcitabine, and wherein the administration of IT-139, or a pharmaceutically acceptable composition thereof, results in a reduction in an amount of GRP78 as compared to administration of gemcitabine alone.

2. The method according to claim 1, wherein the IT-139, or a pharmaceutically acceptable composition thereof, is administered in combination with gemcitabine.

3. The method according to claim 1, wherein the IT-139, or a pharmaceutically acceptable composition thereof, is administered to the patient after gemcitabine is administered to the patient.

4. The method according to claim 1, wherein the IT-139, or a pharmaceutically acceptable composition thereof, is administered to the patient simultaneously with the gemcitabine.

5. The method according to claim 1, wherein the IT-139, or a pharmaceutically acceptable composition thereof, and the gemcitabine are administered to the patient within about 24 hours of each other.

6. The method according to claim 1, wherein the IT-139, or a pharmaceutically acceptable composition thereof, is administered to the patient before the gemcitabine is administered to the patient.

7. The method according to claim 1, wherein the IT-139, or a pharmaceutically acceptable composition thereof, is administered to the patient at least about 12 hours before the gemcitabine is administered to the patient.

8. The method according to claim 1, wherein the IT-139, or a pharmaceutically acceptable composition thereof, is administered to the patient at least about 24 hours before the gemcitabine is administered to the patient.

9. The method according to claim 1, wherein the IT-139, or a pharmaceutically acceptable composition thereof, is administered to the patient at least about 48 hours before the gemcitabine is administered to the patient.

10. The method according to claim 1, wherein the adenocarcinoma is a lung adenocarcinoma.

* * * * *